(12) United States Patent
Targan et al.

(10) Patent No.: US 9,305,137 B1
(45) Date of Patent: Apr. 5, 2016

(54) METHODS OF IDENTIFYING THE GENETIC BASIS OF A DISEASE BY A COMBINATORIAL GENOMICS APPROACH, BIOLOGICAL PATHWAY APPROACH, AND SEQUENTIAL APPROACH

(75) Inventors: Stephan R. Targan, Santa Monica, CA (US); Jerome I. Rotter, Los Angeles, CA (US); Kent D. Taylor, Ventura, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 793 days.

(21) Appl. No.: 12/122,490

(22) Filed: May 16, 2008

Related U.S. Application Data

(60) Provisional application No. 60/938,796, filed on May 18, 2007, provisional application No. 60/939,568, filed on May 22, 2007.

(51) Int. Cl.
*G01N 33/48* (2006.01)
*G06F 19/00* (2011.01)

(52) U.S. Cl.
CPC ..................... *G06F 19/34* (2013.01)

(58) Field of Classification Search
CPC ....................................................... G06F 19/34
USPC .......................................................... 702/19
See application file for complete search history.

(56) References Cited

U.S. PATENT DOCUMENTS

| | | | |
|---|---|---|---|
| 6,858,391 | B2 | 2/2005 | Nunez et al. |
| 7,252,971 | B2 | 8/2007 | Benson et al. |
| 7,332,156 | B2 | 2/2008 | Bowman et al. |
| 2004/0213761 | A1 | 10/2004 | Bowman et al. |
| 2005/0143333 | A1 | 6/2005 | Richards et al. |
| 2005/0163764 | A1 | 7/2005 | Medzhitov et al. |
| 2005/0182007 | A1 | 8/2005 | McSwiggen et al. |
| 2005/0261219 | A1 | 11/2005 | Richards et al. |
| 2006/0067936 | A1 | 3/2006 | Benson et al. |
| 2006/0154276 | A1 | 7/2006 | Lois et al. |
| 2007/0254850 | A1 | 11/2007 | Lieberman et al. |
| 2008/0038831 | A1 | 2/2008 | Benson et al. |
| 2008/0095775 | A1 | 4/2008 | Lewis et al. |
| 2008/0108713 | A1 | 5/2008 | Begovich et al. |
| 2008/0131887 | A1 | 6/2008 | Stephan et al. |
| 2009/0258848 | A1 * | 10/2009 | Chakravarti et al. .......... 514/177 |

OTHER PUBLICATIONS

Yang et al. Intracellular adhesion molecule 1 gene associations with immunologic subsets of inflammatory bowel disease. Gastroenterology, 1995, vol. 109, pp. 440-448.*
Braun et al. Chapter 13: Multiparameter analysis of immunogenetic mechanisms in clinical diagnosis and management of inflammatory bowel disease. Immune Mechanisms in Inflammatory Bowel Disease, edited by Richard S. Blumberg and Markus F. Neurath; Mar. 10, 2006, Springer, first edition, pp. 209-218.*
Email from James Jenkins referencing the "Amazon.com" website regarding exact publication date of "Immune Mechanisms in Inflammatory Bowel Disease, edited by Richard S. Blumberg and Markus F. Neurath; Springer, first edition." Received on Dec. 15, 2010, 2 pages.*
Duerr et al. Linkage and association between inflammatory bowel disease and a locus on chromosome 12. American Journal of Human Genetics, 1998, vol. 63, pp. 95-100.*
Shovman et al. Evaluation of the BioPlex 2200 ANA Screen: Analysis of 510 healthy subjects: Incidence of natural/predictive autoantibodies. Annals of the New York Academy of Science, 2005, vol. 1050, pp. 380-388.*
Ogura, Y. et al., A frameshift mutation in NOD2 associated with susceptibility to Crohn's disease, Nature, 2001, vol. 411, pp. 603-606.
Vermeire, S. et al., Current Status of genetics research in inflammatory bowel disease, Genes and immunity, 2005,6:637-645.

* cited by examiner

*Primary Examiner* — Jerry Lin
(74) *Attorney, Agent, or Firm* — Seth D. Levy; BinQuan Zhuang; Nixon Peabody LLP

(57) ABSTRACT

In one embodiment, the invention provides methods of identifying genes and genetic variants that, either alone or in combination, are important to the pathogenesis of a disease. In another embodiment, the disease is stratified by use of an immune response to disease-associated antigens. In another embodiment, the invention provides methods of identifying pathways that, either alone or in combination, are important to the pathogenesis of a disease. In another embodiment, the invention provides a method of diagnosing or predicting susceptibility to a disease in an individual by determining the presence or absence of genes and genetic variants that, either alone or in combination, are important to the pathogenesis of the disease.

8 Claims, 41 Drawing Sheets

FIG. 4
(PRIOR ART)

| Organism | Antigen | Name |
|---|---|---|
| Saccharomyces | Oligosaccharide | ASCA |
| Commensal bacteria | Neutrophil nucleus | pANCA |
| E. Coli | Outer Membrane Porin C | Anti-OMPC |
| Pseudomonas fluorescens | I-2 sequence | Anti I2 |
| Clostridium sp. | Flagellin | Anti-CBir |

FIG. 5
(PRIOR ART)

| | SB | Fibrosten. | Int. Perf. | SB Surg. | UC-like |
|---|---|---|---|---|---|
| Anti-I2 | - | P=0.027 | - | P<0.03 | - |
| Anti-OmpC | - | - | P<0.02 | - | - |
| ASCA | P=0.003 | P=0.0001 | P=0.0008 | P=0.0007 | P=0.0002 |
| NOD2 | P<0.03 | - | - | - | P<0.05 |
| Anti-Cbir1 | P=0.018 | P=0.05 | P=0.008 | - | - |

| ASCA | Anti-CBir1 |
|---|---|
| Permeability/adherins<br>PTPRB | Myeloid activity<br>PTPRG (IFNγ) |
| Endosomal transport<br>EHD3 | TCR activation<br>TCRα, PTPRC, MGAT5 |
| Innate channel<br>KCNMA1 (CGD mimic) | Transactivation<br>IκBAP "NFκB", Fib, RA17 |
| TCR co-activation<br>BTNL2, PAK7 | Endothelial response<br>ZF124 |
| Cell activation<br>RAC/CDC42 SRGAP3 | |

| CHR | position.dbs np126 | SNP | Import-ance | p-value by permutation | ANTI-BODY | MEASURE-MENT | TRANS-FORM. | gene.id | genes | gene::description |
|---|---|---|---|---|---|---|---|---|---|---|
| 1 | 10737525 | rs205483 | XXXXX | 0.000001 | anti-I2 | PRESENCE ABSENCE | | 54897 | CASZ1 | castor zinc finger 1 |
| 1 | 10737525 | rs205483 | xxx | 0.00005848 | ALL | SUM | QUARTILE | 54897 | CASZ1 | castor zinc finger 1 |
| 1 | 18449300 | rs223198 | xxx | 0.00004237 | IgG | LEVEL | | 84966 | IGSF21 | immunoglobin superfamily, member 21 |
| 1 | 18449300 | rs223198 | xxx | 0.00004932 | IgG | LEVEL | LOGARITHMIC | 84966 | IGSF21 | immunoglobin superfamily, member 21 |
| 1 | 111828556 | rs1361133 | xxx | 0.00005289 | anti-OMPC | PRESENCE ABSENCE | | 140 | ADORA3 | adenosine A3 receptor |
| 1 | 215319172 | rs1553347 | xxx | 0.000018 | ASCA | PRESENCE ABSENCE | | 2104 | ESRRG | estrogen-related receptor gamma |
| 1 | 215319172 | rs1553347 | XXXXX | 0.000001 | IgA | PRESENCE ABSENCE | | 2104 | ESRRG | estrogen-related receptor gamma |
| 1 | 215319172 | rs1553347 | xxx | 0.000026 | IgA | LEVEL | LOGARITHMIC | 2104 | ESRRG | estrogen-related receptor gamma |
| 1 | 230576628 | rs3120767 | xxx | 0.00006873 | anti-I2 | PRESENCE ABSENCE | | 57568 | SIPA1L2 | signal-induced proliferation-associated 1 like 2 |
| 1 | 230580289 | rs789358 | XXXXX | 0.000002 | anti-I2 | PRESENCE ABSENCE | | 57568 | SIPA1L2 | signal-induced proliferation-associated 1 like 2 |
| 2 | 10374017 | rs6709696 | xxx | 0.00005155 | anti-OMPC | PRESENCE ABSENCE | | 3241 | HPCAL1 | hippocalcin-like 1 |
| 2 | 66174003 | rs7597203 | xxx | 0.00004957 | ASCA | PRESENCE ABSENCE | | 440867 | FLJ16124 | FLJ16124 protein |
| 2 | 70027133 | rs10496176 | XXXXX | 0.000008 | IgG | LEVEL | | 4084 | MXD1 | MAX dimerization protein 1 |
| 2 | 70027133 | rs10496176 | xxx | 0.00009543 | IgG | LEVEL | LOGARITHMIC | 4084 | MXD1 | MAX dimerization protein 1 |

FIG. 10B

| | | | | | | | | | |
|---|---|---|---|---|---|---|---|---|---|
| 2 | 79794682 | rs6725030 | xxx | 0.00005753 | IgA | LEVEL | 1496 | CTNNA2 | catenin (cadherin-associated protein), alpha 2 |
| 2 | 101709494 | rs6543092 | xxx | 0.00006515 | ASCA | PRESENCE ABSENCE | 9448 | MAP4K4 | mitogen-activated protein kinase kinase kinase kinase 4 |
| 2 | 101769603 | rs4616501 | xxx | 0.00008511 | ASCA | PRESENCE ABSENCE | 9448 | MAP4K4 | mitogen-activated protein kinase kinase kinase kinase 4 |
| 2 | 202209693 | rs1208081 | xxx | 0.00008761 | ALL | SUM | 65062 | ALS2CR4 | amyotrophic lateral sclerosis 2 (juvenile) chromosome region, candidate 4 |
| 2 | 223457806 | rs705727 | xxx | 0.00007843 | ALL | SUM | 2181 | ACSL3 | acyl-CoA synthetase long-chain family member 3 |
| 2 | 223457806 | rs705727 | xxx | 0.00007477 | ALL | QUARTILE | 2181 | ACSL3 | acyl-CoA synthetase long-chain family member 3 |
| 3 | 4722360 | rs13313995 | xxx | 0.000032 | anti-CBir1 | PRESENCE ABSENCE | 3708 | ITPR1 | inositol 1,4,5-triphosphate receptor, type 1 |
| 3 | 10421826 | rs2160871 | xxx | 0.00007648 | IgG | LEVEL | 491 | ATP2B2 | ATPase, Ca++ transporting, plasma membrane 2 |
| 3 | 41433642 | rs9872216 | xxx | 0.00004723 | IgG | LEVEL | 54986 | ULK4 | unc-51-like kinase 4 (C. elegans) |
| 3 | 54956017 | rs1878110 | xxx | 0.00004556 | anti-CBir1 | PRESENCE ABSENCE | 55799 | CACNA2D3 | calcium channel, voltage-dependent, alpha 2/delta 3 subunit |
| 3 | 98889288 | rs13318801 | xxx | 0.00005618 | IgG | LEVEL | 285220 | EPHA6 | EPH receptor A6 |
| 3 | 121077178 | rs3108749 | xxx | 0.000017 | IgG | LEVEL | 2932 | GSK3B | glycogen synthase kinase 3 beta |
| 3 | 121078193 | rs1719895 | xxx | 0.000017 | IgG | LOGARITHMIC LEVEL | 2932 | GSK3B | glycogen synthase kinase 3 beta |

FIG. 10C

| Chr | Position | | p-value | Marker | Type | Transform | Gene ID | Symbol | Description |
|---|---|---|---|---|---|---|---|---|---|
| 3 | 157721229 | rs4254605 | xxx | 0.0000796 | anti-CBir1 | PRESENCE ABSENCE | | 7881 | KCNAB1 | potassium voltage-gated channel, shaker-related subfamily, beta member 1 |
| 3 | 159311016 | rs111713363 | xxx | 0.00004057 | anti-I2 | PRESENCE ABSENCE | | 51319 | RSRC1 | arginine/serine-rich coiled-coil 1 |
| 3 | 159311016 | rs111713363 | xxx | 0.00004608 | ALL | SUM | QUARTILE | 51319 | RSRC1 | arginine/serine-rich coiled-coil 1 |
| 3 | 159490501 | rs1210359 | xxx | 0.00009592 | anti-I2 | PRESENCE ABSENCE | | 51319 | RSRC1 | arginine/serine-rich coiled-coil 1 |
| 3 | 186392827 | rs11919970 | xxx | 0.000016 | anti-I2 | PRESENCE ABSENCE | | 1962 | EHHADH | enoyl-Coenzyme A, hydratase/3-hydroxyacyl Coenzyme A dehydrogenase |
| 3 | 193394497 | rs12488465 | xxx | 0.00007612 | IgG | PRESENCE ABSENCE | | 2257 | FGF12 | fibroblast growth factor 12 |
| 3 | 195562211 | rs13070515 | xxx | 0.00009256 | ASCA | PRESENCE ABSENCE | | 131578 | LRRC15 | leucine rich repeat containing 15 |
| 4 | 4321627 | rs7671899 | xxx | 0.000012 | anti-I2 | LEVEL | | 55646 | LYAR | hypothetical protein FLJ20425 |
| 4 | 5503796 | rs7678335 | xxx | 0.00007812 | IgG | LEVEL | | 55351 | STK32B | serine/threonine kinase 32B |
| 4 | 5503796 | rs7678335 | xxx | 0.00008048 | IgG | LEVEL | LOGARITHMIC | 55351 | STK32B | serine/threonine kinase 32B |
| 4 | 5513915 | rs1034748 | xxx | 0.00006468 | IgG | LEVEL | LOGARITHMIC | 55351 | STK32B | serine/threonine kinase 32B |
| 4 | 16094104 | rs872182 | XXXXX | 0.000006 | ALL | SUM | ADJUSTED | 9079 | LDB2 | LIM domain binding 2 |
| 4 | 16094104 | rs872182 | xxx | 0.000026 | ALL | SUM | QUARTILE | 9079 | LDB2 | LIM domain binding 2 |
| 4 | 46701156 | rs13139021 | XXXXX | 0.000004 | anti-CBir1 | PRESENCE ABSENCE | | 2557 | GABRA4 | gamma-aminobutyric acid (GABA) A receptor, alpha 4 |

FIG. 10D

| chr | pos | rs | | p-value | antibody | type | | gene ID | symbol | description |
|---|---|---|---|---|---|---|---|---|---|---|
| 4 | 74936965 | rs872914 | xxx | 0.00007484 | IgA | PRESENCE ABSENCE | | 5197 | PF4V1 | platelet factor 4 variant 1 |
| 4 | 82103746 | rs1052325 | xxx | 0.00005731 | IgA | LEVEL | | 255119 | C4orf22 | chromosome 4 open reading frame 22 |
| 4 | 96612588 | rs265060 | xxx | 0.00009921 | IgA | LEVEL | | 8633 | UNC5C | unc-5 homolog C (C. elegans) |
| 4 | 96612588 | rs265060 | xxx | 0.00008529 | ALL | SUM | ADJUSTED | 8633 | UNC5C | unc-5 homolog C (C. elegans) |
| 4 | 96612588 | rs265060 | xxx | 0.00009569 | ALL | SUM | QUARTILE | 8633 | UNC5C | unc-5 homolog C (C. elegans) |
| 4 | 137939936 | rs17829074 | xxx | 0.000015 | ALL | SUM | ADJUSTED | 729578 | LOC729578 | hypothetical protein LOC729578 |
| 4 | 137939936 | rs17829074 | xxx | 0.00001 | ALL | SUM | QUARTILE | 729578 | LOC729578 | hypothetical protein LOC729578 |
| 4 | 180158677 | rs2167371 | XXXXX | 0.000004 | anti-OMPC | LEVEL | | | BC043428 | |
| 4 | 185323707 | rs2310044 | xxx | 0.000039 | ALL | SUM | ADJUSTED | 133121 | ENPP6 | ectonucleotide pyrophosphatase/phosphodiesterase 6 |
| 4 | 185323707 | rs2310044 | xxx | 0.000011 | ALL | SUM | QUARTILE | 133121 | ENPP6 | ectonucleotide pyrophosphatase/phosphodiesterase 6 |
| 5 | 32028979 | rs2052852 | xxx | 0.00009752 | ASCA | PRESENCE ABSENCE | | 23037 | PDZD2 | PDZ domain containing 2 |
| 5 | 32028979 | rs2052852 | xxx | 0.000027 | IgG | PRESENCE ABSENCE | | 23037 | PDZD2 | PDZ domain containing 2 |
| 5 | 39154979 | rs427829 | xxx | 0.00008501 | IgA | LEVEL | LOGARITHMIC | 2533 | FYB | FYN binding protein (FYB-120/130) |
| 5 | 76657430 | rs3797462 | xxx | 0.00006927 | anti-OMPC | PRESENCE ABSENCE | | 8622 | PDE8B | phosphodiesterase 8B |
| 5 | 80665128 | rs6881927 | xxx | 0.00008685 | anti-CBir1 | LEVEL | LOGARITHMIC | 134526 | ACOT12 | acyl-CoA thioesterase 12 |
| 5 | 92370602 | rs2453759 | xxx | 0.00005472 | IgG | LEVEL | LOGARITHMIC | | BG204737 | |

FIG. 10E

| Chr | Position | RS | | p-value | Marker | Type | Method | Gene ID | Symbol | Description |
|---|---|---|---|---|---|---|---|---|---|---|
| 5 | 117559122 | rs2061882 | xxx | 0.00009235 | ALL | SUM | QUARTILE | BX098718, BG208476 | | |
| 5 | 133892498 | rs329122 | xxx | 0.00006309 | anti-CBir1 | PRESENCE ABSENCE | | 23338 | PHF15 | PHD finger protein 15 |
| 5 | 138131165 | rs851278 | xxx | 0.00005745 | anti-CBir1 | PRESENCE ABSENCE | | 1495 | CTNNA1 | catenin (cadherin-associated protein), alpha 1, 102kDa |
| 5 | 138254666 | rs176382 | xxx | 0.000031 | anti-CBir1 | PRESENCE ABSENCE | | 1495 | CTNNA1 | catenin (cadherin-associated protein), alpha 1, 102kDa |
| 5 | 138269217 | rs12719515 | xxx | 0.00004587 | anti-CBir1 | PRESENCE ABSENCE | | 1495 | CTNNA1 | catenin (cadherin-associated protein), alpha 1, 102kDa |
| 5 | 141385691 | rs163918 | xxx | 0.00008648 | IgG | LEVEL | LOGARITHMIC | 10007 | GNPDA1 | glucosamine-6-phosphate deaminase 1 |
| 5 | 147102213 | rs6895278 | xxx | 0.00006039 | IgG | LEVEL | | 9832 | JAKMIP2 | janus kinase and microtubule interacting protein 2 |
| 5 | 167753560 | rs2112555 | xxx | 0.00006568 | ALL | SUM | ADJUSTED | 23286 | WWC1 | WW and C2 domain containing 1 |
| 5 | 167753560 | rs2112555 | xxx | 0.00006126 | ALL | SUM | QUARTILE | 23286 | WWC1 | WW and C2 domain containing 1 |
| 5 | 174793846 | rs265974 | XXXXX | 0.000005 | ALL | SUM | ADJUSTED | 1812 | DRD1 | dopamine receptor D1 |
| 5 | 174793846 | rs265974 | xxx | 0.000026 | ALL | SUM | QUARTILE | 1812 | DRD1 | dopamine receptor D1 |
| 5 | 177611132 | rs6422346 | xxx | 0.00008299 | ALL | SUM | ADJUSTED | 91522 | COL23A1 | collagen, type XXIII, alpha 1 |
| 5 | 177611132 | rs6422346 | xxx | 0.00005096 | ALL | SUM | QUARTILE | 91522 | COL23A1 | collagen, type XXIII, alpha 1 |
| 6 | 461350 | rs2493013 | xxx | 0.000036 | anti-I2 | PRESENCE ABSENCE | | 55770 | EXOC2 | exocyst complex component 2 |
| 6 | 7678861 | rs6910759 | XXXXX | 0.000005 | ALL | SUM | ADJUSTED | 654 | BMP6 | bone morphogenetic protein 6 |

FIG. 10F

| | | | | | | | | |
|---|---|---|---|---|---|---|---|---|
| 6 | 7678861 | rs6910759 | XXXXX | 0.000009 | ALL | SUM | QUARTILE | | bone morphogenetic protein 6 |
| 6 | 15174703 | rs3846947 | XXXXX | 0.000001 | anti-OMPC | LEVEL | | 728961 BMP6 | hypothetical protein LOC728961 |
| 6 | 16470367 | rs179973 | | 0.0001361 | ALL | SUM | ADJUSTED QUARTILE | 728961 LOC728961 | ataxin 1 |
| 6 | 16470367 | rs179973 | xxx | 0.00008447 | ALL | SUM | | 6310 ATXN1 | ataxin 1 |
| 6 | 31164808 | rs2523849 | XXXXX | 0.000002 | IgG | LEVEL | | 6310 ATXN1 | |
| 6 | 31167273 | rs2428514 | xxx | 0.00009132 | IgG | PRESENCE ABSENCE | | FLJ37114 | |
| 6 | 31167273 | rs2428514 | XXXXX | 0.000001 | IgG | LEVEL | | FLJ37114 | |
| 6 | 31167273 | rs2428514 | xxx | 0.000032 | IgG | LEVEL | | FLJ37114 | |
| 6 | 31222115 | rs6917517 | xxx | 0.00006814 | IgA | LEVEL | LOGARITHMIC | FLJ37114 | |
| 6 | 31222115 | rs6917517 | xxx | 0.00004338 | IgG | LEVEL | | 170679 CDSN,PSO RS1C1 | psoriasis susceptibility 1 candidate 1 |
| 6 | 31222115 | rs6917517 | xxx | 0.000038 | IgG | LEVEL | LOGARITHMIC | 170679 CDSN,PSO RS1C1 | psoriasis susceptibility 1 candidate 1 |
| 6 | 31223924 | rs1042127 | xxx | 0.00006126 | IgA | LEVEL | | 170679 CDSN,PSO RS1C1 | psoriasis susceptibility 1 candidate 1 |
| 6 | 31223924 | rs1042127 | xxx | 0.000035 | IgG | LEVEL | | 170679 CDSN,PSO RS1C1 | psoriasis susceptibility 1 candidate 1 |
| 6 | 31223924 | rs1042127 | xxx | 0.000029 | IgG | LEVEL | LOGARITHMIC | 170679 CDSN,PSO RS1C1 | psoriasis susceptibility 1 candidate 1 |
| 6 | 31973245 | rs644827 | xxx | 0.00007767 | ALL | SUM | QUARTILE | 170679 CDSN,PSO RS1C1 | psoriasis susceptibility 1 candidate 1 |
| 6 | 31974113 | rs2242665 | xxx | 0.00007767 | ALL | SUM | QUARTILE | 80736 SLC44A4 | solute carrier family 44, member 4 |
| 6 | 32057060 | rs630379 | xxx | 0.00005789 | IgG | LEVEL | | 80736 SLC44A4 | solute carrier family 44, member 4 |
| | | | | | | | | 7936 RDBP | RD RNA binding protein |

FIG. 10G

| Chr | Position | RS | | p-value | Ig | Type | Transform | Gene ID | Symbol | Gene name |
|---|---|---|---|---|---|---|---|---|---|---|
| 6 | 32057060 | rs630379 | xxx | 0.00005632 | ALL | SUM | QUARTILE | 7936 | RDBP | RD RNA binding protein |
| 6 | 32475662 | rs31299963 | xxx | 0.00008147 | IgG | PRESENCE ABSENCE | | 56244 | BTNL2 | butyrophilin-like 2 (MHC class II associated) |
| 6 | 32477389 | rs743862 | xxxxx | 0.000007 | IgG | PRESENCE ABSENCE | | 56244 | BTNL2 | butyrophilin-like 2 (MHC class II associated) |
| 6 | 32477389 | rs743862 | xxx | 0.000015 | IgG | LEVEL | | 56244 | BTNL2 | butyrophilin-like 2 (MHC class II associated) |
| 6 | 32500379 | rs2395174 | xxx | 0.00008483 | IgG | PRESENCE ABSENCE | | 3122 | HLA-DRA | major histocompatibility complex, class II, DR alpha |
| 6 | 32507025 | rs2239804 | xxx | 0.000037 | IgG | LEVEL | | 3122 | HLA-DRA | major histocompatibility complex, class II, DR alpha |
| 6 | 32523248 | rs9268832 | xxx | 0.00004767 | IgG | PRESENCE ABSENCE | | 3122 | HLA-DRA | major histocompatibility complex, class II, DR alpha |
| 6 | 32721640 | rs9275141 | xxx | 0.00005745 | IgG | PRESENCE ABSENCE | | | HLA-DQB1 | |
| 6 | 32734983 | rs2647012 | xxx | 0.00002 | IgG | PRESENCE ABSENCE | | | HLA-DQB1 | |
| 6 | 36117361 | rs851021 | xxx | 0.00005997 | IgA | LEVEL | | 1432 | MAPK14 | mitogen-activated protein kinase 14 |
| 6 | 39227815 | rs7773754 | xxx | 0.00006299 | IgA | LEVEL | | | AK055788 | |
| 6 | 71974318 | rs12661758 | xxx | 0.000015 | IgG | LEVEL | LOGARITHMIC | | DB234735 | |
| 6 | 71979436 | rs9346446 | xxx | 0.00002 | IgG | LEVEL | LOGARITHMIC | | DB234735 | |
| 6 | 89961591 | rs453561 | xxx | 0.00004499 | ALL | SUM | ADJUSTED | 2569 | GABRR1 | gamma-aminobutyric acid (GABA) receptor, rho 1 |
| 6 | 89961591 | rs453561 | xxx | 0.000012 | ALL | SUM | QUARTILE | 2569 | GABRR1 | gamma-aminobutyric acid (GABA) receptor, rho 1 |

FIG. 10H

| | | | | | | | | | | |
|---|---|---|---|---|---|---|---|---|---|---|
| 6 | 130053359 | rs11154491 | xxx | 0.00007929 | IgG | LEVEL | | 93663 | ARHGAP18 | Rho GTPase activating protein 18 |
| 6 | 147309970 | rs7742400 | XXXXX | 0.000002 | IgG | PRESENCE ABSENCE | | 729178 | LOC729178 | hypothetical protein LOC729178 |
| 6 | 147309970 | rs7742400 | xxx | 0.000023 | IgG | LEVEL | | 729178 | LOC729178 | hypothetical protein LOC729178 |
| 6 | 158331352 | rs9459056 | XXXXX | 0.000004 | IgA | LEVEL | | 8871 | SYNJ2 | synaptojanin 2 |
| 6 | 158331352 | rs9459056 | xxx | 0.00005571 | IgA | LEVEL | LOGARITHMIC | 8871 | SYNJ2 | synaptojanin 2 |
| 6 | 167003680 | rs6921577 | xxx | 0.00007339 | anti-OMPC | LEVEL | | 6196 | RPS6KA2 | ribosomal protein S6 kinase, 90kDa, polypeptide 2 |
| 7 | 3735416 | rs12701014 | xxx | 0.00004489 | IgG | LEVEL | | 221935 | SDK1 | sidekick homolog 1, cell adhesion molecule (chicken) |
| 7 | 31982261 | rs7808892 | xxx | 0.00008556 | anti-I2 | PRESENCE ABSENCE | | 5137 | PDE1C | phosphodiesterase 1C, calmodulin-dependent 70kDa |
| 7 | 105510257 | rs17153258 | xxx | 0.000059 | anti-CBir1 | LEVEL | | | AF086203 | |
| 7 | 105517818 | rs6975426 | xxx | 0.00004896 | anti-CBir1 | LEVEL | | | AF086203 | |
| 7 | 153294558 | rs4628181 | xxx | 0.0000518 | anti-OMPC | PRESENCE ABSENCE | | 1804 | DPP6 | dipeptidyl-peptidase 6 |
| 8 | 3261623 | rs6996823 | xxx | 0.00008214 | anti-OMPC | LEVEL | | 64478 | CSMD1 | CUB and Sushi multiple domains 1 |
| 8 | 18425515 | rs10090117 | xxx | 0.00004545 | IgA | LEVEL | | 23362 | PSD3 | pleckstrin and Sec7 domain containing 3 |
| 8 | 23258190 | rs11774789 | xxx | 0.00008475 | ALL | SUM | ADJUSTED | 4017 | LOXL2 | lysyl oxidase-like 2 |
| 8 | 24925353 | rs2976456 | XXXXX | 0.000002 | anti-OMPC | LEVEL | | 4747 | NEFL | neurofilament, light polypeptide 68kDa |
| 8 | 24987230 | rs11135841 | XXXXX | 0.000001 | anti-OMPC | LEVEL | | 4747 | NEFL | neurofilament, light polypeptide 68kDa |
| 8 | 38671914 | rs7816405 | XXXXX | 0.000009 | anti-CBir1 | LEVEL | | | BX091769 | |
| 8 | 38691579 | rs6983695 | xxx | 0.00006536 | anti-CBir1 | LEVEL | | | BX091769 | |

FIG. 10I

| | | | | | | | |
|---|---|---|---|---|---|---|---|
| 8 | 83590018 | rs10504762 | xxx | 0.000015 | IgG | LEVEL | LOGARITHMIC | 389674 | HNRPA1P4 | heterogeneous nuclear ribonucleoprotein A1 pseudogene 4 |
| 8 | 108447077 | rs2163870 | xxx | 0.00007678 | IgG | LEVEL | LOGARITHMIC | 284 | ANGPT1 | angiopoietin 1 |
| 8 | 108559172 | rs951759 | xxx | 0.000028 | IgG | PRESENCE ABSENCE | | 284 | ANGPT1 | angiopoietin 1 |
| 9 | 1028010 | rs884101 | xxx | 0.000022 | ALL | SUM | ADJUSTED | 10655 | DMRT2 | doublesex and mab-3 related transcription factor 2 |
| 9 | 1028010 | rs884101 | xxx | 0.000017 | ALL | SUM | QUARTILE | 10655 | DMRT2 | doublesex and mab-3 related transcription factor 2 |
| 9 | 1031524 | rs2279989 | xxx | 0.000024 | ALL | SUM | ADJUSTED | 10655 | DMRT2 | doublesex and mab-3 related transcription factor 2 |
| 9 | 1031524 | rs2279989 | xxx | 0.000019 | ALL | SUM | QUARTILE | 10655 | DMRT2 | doublesex and mab-3 related transcription factor 2 |
| 9 | 10468387 | rs2784624 | xxx | 0.000029 | IgA | PRESENCE ABSENCE | | 5789 | PTPRD | protein tyrosine phosphatase, receptor type, D |
| 9 | 10468387 | rs2784624 | XXXXX | 0.000006 | IgA | LEVEL | | 5789 | PTPRD | protein tyrosine phosphatase, receptor type, D |
| 9 | 10468387 | rs2784624 | xxx | 0.000018 | IgA | LEVEL | LOGARITHMIC | 5789 | PTPRD | protein tyrosine phosphatase, receptor type, D |
| 9 | 28045900 | rs1901565 | xxx | 0.000019 | IgG | LEVEL | | | LRRN6C | |
| 9 | 28045900 | rs1901565 | xxx | 0.00004146 | IgG | LEVEL | LOGARITHMIC | | LRRN6C | |
| 9 | 99945479 | rs3780465 | xxx | 0.00006684 | anti-CBir1 | LEVEL | | 7464 | CORO2A | coronin, actin binding protein, 2A |
| 9 | 99953197 | rs2795492 | XXXXX | 0.000001 | anti-CBir1 | LEVEL | | 7464 | CORO2A | coronin, actin binding protein, 2A |

FIG. 10J

| | | | | | | | | |
|---|---|---|---|---|---|---|---|---|
| 9 | 116376698 | rs10982300 | xxx | 0.00008998 | anti-CBir1 | PRESENCE ABSENCE | | 9550 | ATP6V1G1 | ATPase, H+ transporting, lysosomal 13kDa, V1 subunit G1 |
| 9 | 116446202 | rs2183018 | xxx | 0.00005848 | anti-CBir1 | PRESENCE ABSENCE | | 203197 | C9orf91 | chromosome 9 open reading frame 91 |
| 9 | 116446422 | rs1058278 | xxx | 0.000039 | anti-CBir1 | PRESENCE ABSENCE | | 203197 | C9orf91 | chromosome 9 open reading frame 91 |
| 9 | 116447744 | rs1058280 | xxx | 0.00005848 | anti-CBir1 | PRESENCE ABSENCE | | 203197 | C9orf91 | chromosome 9 open reading frame 91 |
| 9 | 129626509 | rs3739817 | xxx | 0.00008403 | anti-I2 | LEVEL | | 2022 | ENG | endoglin (Osler-Rendu-Weber syndrome 1) |
| 9 | 129697654 | rs3780670 | xxx | 0.000018 | ALL | SUM | ADJUSTED | 30815 | ST6GALNAC6 | ST6 (alpha-N-acetyl-neuraminyl-2,3-beta-galactosyl-1,3)-N-acetylgalactosaminide alpha-2,6-sialyltransferase 6 |
| 9 | 129697654 | rs3780670 | xxx | 0.00004489 | ALL | SUM | QUARTILE | 30815 | ST6GALNAC6 | ST6 (alpha-N-acetyl-neuraminyl-2,3-beta-galactosyl-1,3)-N-acetylgalactosaminide alpha-2,6-sialyltransferase 6 |
| 9 | 136703513 | rs4842139 | xxx | 0.00005391 | anti-OMPC | LEVEL | | 1289 | COL5A1 | collagen, type V, alpha 1 |
| 9 | 137288987 | rs7858253 | xxx | 0.00008155 | IgG | LEVEL | | | BG437415 | |
| 9 | 137333104 | rs10858383 | xxx | 0.000035 | IgA | LEVEL | | | C9orf62 | |
| 9 | 137335350 | rs10858385 | xxx | 0.00007984 | ALL | SUM | LOGARITHMIC | | C9orf62 | |
| 9 | 137335350 | rs10858385 | xxxxxx | 0.000005 | IgA | LEVEL | ADJUSTED | | C9orf62 | |
| 9 | 137335350 | rs10858385 | xxx | 0.00008439 | IgG | LEVEL | LOGARITHMIC | | C9orf62 | |
| 9 | 4560425 | rs10795184 | xxx | 0.00008978 | anti-CBir1 | LEVEL | LOGARITHMIC | | CR749391 | |
| 10 | 33883553 | rs2804875 | xxx | 0.000032 | anti-OMPC | LEVEL | | 8829 | NRP1 | neuropilin 1 |

FIG. 10K

| | | | | | | | |
|---|---|---|---|---|---|---|---|
| 10 | 53478604 | rs1871080 | xxx | 0.00009877 | anti-CBir1 | PRESENCE ABSENCE | | 5592 | PRKG1 | protein kinase, cGMP-dependent, type I |
| 10 | 59174553 | rs11591417 | xxx | 0.000025 | anti-OMPC | LEVEL | | | CB269818 | |
| 10 | 59277608 | rs6481369 | xxx | 0.00005006 | anti-OMPC | LEVEL | | | CB269818 | |
| 10 | 73442768 | rs730720 | xxx | 0.00004545 | IgA | PRESENCE ABSENCE | | 9469 | CHST3 | carbohydrate (chondroitin 6) sulfotransferase 3 |
| 10 | 73445713 | rs896076 | xxx | 0.000037 | IgA | PRESENCE ABSENCE | | 9469 | CHST3 | carbohydrate (chondroitin 6) sulfotransferase 3 |
| 10 | 73445713 | rs896076 | xxx | 0.00008667 | IgA | LEVEL | | 9469 | CHST3 | carbohydrate (chondroitin 6) sulfotransferase 3 |
| 10 | 78964686 | rs7921994 | xxx | 0.00008723 | IgG | LEVEL | LOGARITHMIC | 3778 | KCNMA1 | potassium large conductance calcium-activated channel, subfamily M, alpha member 1 |
| 10 | 78992459 | rs2619641 | xxx | 0.00008574 | ALL | SUM | ADJUSTED | 3778 | KCNMA1 | potassium large conductance calcium-activated channel, subfamily M, alpha member 1 |
| 10 | 79750872 | rs7920472 | xxx | 0.000026 | ALL | SUM | ADJUSTED | | AF086162 | |
| 10 | 79750872 | rs7920472 | xxx | 0.00004566 | ALL | SUM | QUARTILE | | AF086162 | |
| 10 | 79936245 | rs2099517 | xxx | 0.00007387 | IgG | LEVEL | | | AF086162 | |
| 10 | 85122464 | rs4418744 | xxx | 0.000099625 | anti-OMPC | PRESENCE ABSENCE | | | AK056904 | |
| 10 | 133068612 | rs3123221 | xxx | 0.00005115 | IgG | LEVEL | LOGARITHMIC | 256536 | TCERG1L | transcription elongation regulator 1-like |
| 11 | 1531644 | rs7951820 | xxx | 0.00004756 | ALL | SUM | ADJUSTED | 81532 | HCCA2 | HCCA2 protein |
| 11 | 1531644 | rs7951820 | xxx | 0.00007828 | ALL | SUM | QUARTILE | 81532 | HCCA2 | HCCA2 protein |

FIG. 10L

| Chr | Position | RS | col4 | col5 | Antibody | Type | Transform | Gene ID | Symbol | Description |
|---|---|---|---|---|---|---|---|---|---|---|
| 11 | 2459062 | rs10832134 | xxx | 0.00009205 | ALL | SUM | ADJUSTED | 3784 | KCNQ1 | potassium voltage-gated channel, KQT-like subfamily, member 1 |
| 11 | 6216077 | rs325702 | xxx | 0.000015 | IgG | PRESENCE ABSENCE | | 1262 | CNGA4-CCKBR | cyclic nucleotide gated channel alpha 4 |
| 11 | 6216077 | rs325702 | xxx | 0.00005063 | IgG | LEVEL | | 1262 | CNGA4-CCKBR | cyclic nucleotide gated channel alpha 4 |
| 11 | 6216077 | rs325702 | XXXXX | 0.000007 | IgG | LEVEL | LOGARITHMIC | 1262 | CNGA4-CCKBR | cyclic nucleotide gated channel alpha 4 |
| 11 | 12925354 | rs4469873 | xxx | 0.00004435 | IgG | PRESENCE ABSENCE | | 7003 | TEAD1 | TEA domain family member 1 (SV40 transcriptional enhancer factor) |
| 11 | 46447735 | rs12574250 | xxx | 0.00009453 | ASCA | PRESENCE ABSENCE | | 55626 | FLJ20294 | hypothetical protein FLJ20294 |
| 11 | 48069499 | rs10501322 | xxx | 0.00007663 | anti-OMPC | LEVEL | | 5795 | PTPRJ | protein tyrosine phosphatase, receptor type, J |
| 11 | 55420386 | rs99943659 | xxx | 0.00007018 | anti-OMPC | LEVEL | | 84767 | SPRYD5 | SPRY domain containing 5 |
| 11 | 55447435 | rs7936086 | xxx | 0.00006873 | anti-OMPC | LEVEL | | 10798 | OR5I1 | olfactory receptor, family 5, subfamily I, member 1 |
| 11 | 55452561 | rs7115131 | xxx | 0.00006873 | anti-OMPC | LEVEL | | 10798 | OR5I1 | olfactory receptor, family 5, subfamily I, member 1 |
| 11 | 55459537 | rs9665861 | xxx | 0.00006873 | anti-OMPC | LEVEL | | 10798 | OR5I1 | olfactory receptor, family 5, subfamily I, member 1 |
| 11 | 55460226 | rs9666086 | xxx | 0.00006873 | anti-OMPC | LEVEL | | 10798 | OR5I1 | olfactory receptor, family 5, subfamily I, member 1 |
| 11 | 74106228 | rs968305 | XXXXX | 0.000005 | IgA | PRESENCE ABSENCE | | 25884 | CHRDL2 | chordin-like 2 |
| 11 | 93190216 | rs644009 | xxx | 0.00009533 | IgG | LEVEL | LOGARITHMIC | 9440 | CRSP6 | cofactor required for Sp1 transcriptional activation, subunit 6, 77kDa |

FIG. 10M

| | | | | | | | |
|---|---|---|---|---|---|---|---|
| 11 | 99209253 | rs7129269 | xxx | 0.00009501 | ALL | QUARTILE | 53942 | CNTN5 | contactin 5 |
| 11 | 104403053 | rs557905 | xxx | 0.0000813 | anti-I2 | LEVEL | 834 | CASP1 | caspase 1, apoptosis-related cysteine peptidase (interleukin 1, beta, convertase) |
| 11 | 104409780 | rs568910 | xxx | 0.000091 | anti-I2 | LEVEL | 834 | CASP1 | caspase 1, apoptosis-related cysteine peptidase (interleukin 1, beta, convertase) |
| 11 | 104417668 | rs1503391 | xxx | 0.000091 | anti-I2 | LEVEL | 114769 | COP1 | caspase-1 dominant-negative inhibitor pseudo-ICE |
| 11 | 104423727 | rs7934239 | xxx | 0.000028 | anti-OMPC | LEVEL | 114769 | COP1 | caspase-1 dominant-negative inhibitor pseudo-ICE |
| 11 | 110504638 | rs12276464 | xxx | 0.00005865 | anti-OMPC | PRESENCE ABSENCE | 5450 | POU2AF1 | POU domain, class 2, associating factor 1 |
| 11 | 130890705 | rs385987 | xxx | 0.0000995 | IgA | LEVEL | 50863 | HNT | neurotrimin |
| 12 | 477487 | rs12313707 | xxx | 0.00009886 | ASCA | PRESENCE ABSENCE | 283358 | B4GALNT3 | beta-1,4-N-acetyl-galactosaminyl transferase 3 |
| 12 | 477487 | rs12313707 | xxx | 0.000028 | IgA | PRESENCE ABSENCE | 283358 | B4GALNT3 | beta-1,4-N-acetyl-galactosaminyl transferase 3 |
| 12 | 7440276 | rs4072797 | xxx | 0.00004525 | IgG | LEVEL | 283316 | CD163L1 | CD163 molecule-like 1 |
| 12 | 10742925 | rs2166066 | xxx | 0.00008122 | IgG | LEVEL | 8531 | CSDA | cold shock domain protein A |
| 12 | 10761665 | rs3816566 | xxx | 0.0000979 | ALL | SUM | 8531 | CSDA | cold shock domain protein A |
| 12 | 46326141 | rs1153978 | xxx | 0.000032 | IgG | LEVEL | | FLJ21908 | |
| 12 | 46326141 | rs1153978 | xxx | 0.000015 | IgG | LEVEL | | FLJ21908 | |
| 12 | 46337723 | rs948393 | xxx | 0.00008742 | IgG | LEVEL | | FLJ21908 | |

FIG. 10N

| | | | | | | | | |
|---|---|---|---|---|---|---|---|---|
| 12 | 46337723 | rs948393 | xxx | 0.0000479 | IgG | LEVEL | LOGARITHMIC | 11163 | FLJ21908 | nudix (nucleoside diphosphate linked moiety X)-type motif 4 |
| 12 | 92237010 | rs6538408 | XXXXX | 0.000005 | IgG | LEVEL | | | NUDT4 | |
| 12 | 97719929 | rs1477237 | xxx | 0.00009047 | anti-CBir1 | LEVEL | | 56899 | ANKS1B | ankyrin repeat and sterile alpha motif domain containing 1B |
| 12 | 97719929 | rs1477237 | xxx | 0.0000978 | ALL | SUM | ADJUSTED | 56899 | ANKS1B | ankyrin repeat and sterile alpha motif domain containing 1B |
| 12 | 97719929 | rs1477237 | xxx | 0.000007533 | ALL | SUM | QUARTILE | 56899 | ANKS1B | ankyrin repeat and sterile alpha motif domain containing 1B |
| 12 | 105877725 | rs10746071 | xxx | 0.00004306 | anti-I2 | LEVEL | | | C12orf23,LOC728705 | |
| 12 | 117225058 | rs468574 | xxx | 0.00009466 | IgA | LEVEL | LOGARITHMIC | 51347 | TAOK3 | TAO kinase 3 |
| 13 | 22838710 | rs6490792 | xxx | 0.00005153 | IgA | LEVEL | | 26278 | SACS | spastic ataxia of Charlevoix-Saguenay (sacsin) |
| 13 | 107034232 | rs1998564 | xxx | 0.00005944 | anti-CBir1 | LEVEL | | 728215 | LOC728215 | similar to transmembrane protein 28 |
| 14 | 22967306 | rs1951154 | xxx | 0.00006088 | ALL | SUM | QUARTILE | 4625 | MYH7 | myosin, heavy chain 7, cardiac muscle, beta |
| 14 | 29657679 | rs8011977 | xxx | 0.000033 | IgG | LEVEL | LOGARITHMIC | 5587 | PRKD1 | protein kinase D1 |
| 14 | 29663179 | rs7152980 | xxx | 0.00007561 | IgG | LEVEL | | 5587 | PRKD1 | protein kinase D1 |
| 14 | 29663179 | rs7152980 | xxx | 0.000024 | IgG | LEVEL | LOGARITHMIC | 5587 | PRKD1 | protein kinase D1 |
| 14 | 62259523 | rs11158449 | xxx | 0.00007913 | IgG | PRESENCE ABSENCE | | 27133 | KCNH5 | potassium voltage-gated channel, subfamily H (eag-related), member 5 |
| 15 | 371145001 | rs990579 | xxx | 0.00004008 | anti-OMPC | LEVEL | | | FLJ39531 | |
| 15 | 59900432 | rs8023523 | xxx | 0.000016 | IgA | LEVEL | | 54832 | VPS13C | vacuolar protein sorting 13 homolog C (S. cerevisiae) |

FIG. 10O

| Chr | Position | SNP | | p-value | Antibody | Type | Transformation | Gene ID | Gene Symbol | Gene Name |
|---|---|---|---|---|---|---|---|---|---|---|
| 15 | 59900432 | rs8023523 | xxx | 0.00009602 | IgA | LEVEL | LOGARITHMIC | 54832 | VPS13C | vacuolar protein sorting 13 homolog C (S. cerevisiae) |
| 15 | 78491816 | rs1446337 | XXXXX | 0.000008 | IgG | PRESENCE ABSENCE | | 9915 | ARNT2 | aryl-hydrocarbon receptor nuclear translocator 2 |
| 15 | 90816282 | rs1455775 | xxx | 0.0000489 | ALL | SUM | ADJUSTED | 145858 | C15orf32 | chromosome 15 open reading frame 32 |
| 15 | 90816282 | rs1455775 | xxx | 0.00009975 | ALL | SUM | QUARTILE | 145858 | C15orf32 | chromosome 15 open reading frame 32 |
| 15 | 94629190 | rs8033891 | xxx | 0.000031 | anti-OMPC | LEVEL | | | FLJ10010 | |
| 15 | 94641189 | rs4984430 | XXXXX | 0.000004 | anti-OMPC | LEVEL | | | FLJ10010 | |
| 16 | 6276738 | rs716509 | xxx | 0.000028 | IgA | PRESENCE ABSENCE | | 54715 | A2BP1 | ataxin 2-binding protein 1 |
| 16 | 6276738 | rs716509 | xxx | 0.00009355 | IgA | LEVEL | LOGARITHMIC | 54715 | A2BP1 | ataxin 2-binding protein 1 |
| 16 | 7169331 | rs1922587 | xxx | 0.0000409 | IgG | PRESENCE ABSENCE | | 54715 | A2BP1 | ataxin 2-binding protein 1 |
| 16 | 7175014 | rs1922589 | xxx | 0.000037 | IgG | PRESENCE ABSENCE | | 54715 | A2BP1 | ataxin 2-binding protein 1 |
| 16 | 27047330 | rs4787923 | XXXXX | 0.000009 | IgG | LEVEL | | 3566 | IL4R | interleukin 4 receptor |
| 16 | 27900129 | rs8054996 | xxx | 0.00005298 | anti-OMPC | LEVEL | | | UNQ5831 | |
| 16 | 27910722 | rs4788025 | xxx | 0.000024 | anti-I2 | LEVEL | | | UNQ5831 | |
| 16 | 72153219 | rs825688 | xxx | 0.000019 | ALL | SUM | ADJUSTED | | ng | |
| 16 | 72163783 | rs825678 | xxx | 0.00009183 | anti-I2 | PRESENCE ABSENCE | | | ng | |
| 16 | 77869647 | rs9806910 | xxx | 0.00008732 | IgG | PRESENCE ABSENCE | | 51741 | WWOX | WW domain containing oxidoreductase |
| 16 | 80357386 | rs10445097 | xxx | 0.00007241 | IgG | LEVEL | | 5336 | PLCG2 | phospholipase C, gamma 2 (phosphatidylinositol-specific) |

FIG. 10P

| | | | | | | | |
|---|---|---|---|---|---|---|---|
| 16 | 80357386 | rs10445097 | XXXXX | 0.000009 | IgG | LOGARITHMIC | 5336 | PLCG2 | phospholipase C, gamma 2 (phosphatidylinositol-specific) |
| 17 | 23731073 | rs2027993 | xxx | 0.0000773 | IgG | PRESENCE ABSENCE | 23098 | SARM1 | sterile alpha and TIR motif containing 1 |
| 17 | 35485379 | rs939348 | xxx | 0.00005168 | IgG | LEVEL | 7067 | THRA | thyroid hormone receptor, alpha (erythroblastic leukemia viral (v-erb-a) oncogene homolog, avian) |
| 17 | 39410265 | rs918242 | xxx | 0.000024 | anti-OMPC | PRESENCE ABSENCE | 5697 | PYY | peptide YY |
| 17 | 62233006 | rs7342847 | xxx | 0.00005208 | IgG | PRESENCE ABSENCE | 5578 | PRKCA | protein kinase C, alpha |
| 17 | 62233006 | rs7342847 | XXXXX | 0.000007 | IgG | LEVEL | 5578 | PRKCA | protein kinase C, alpha |
| 17 | 72147848 | rs8069024 | xxx | 0.000026 | IgG | LEVEL | 55808 | ST6GALNAC1 | ST6 (alpha-N-acetyl-neuraminyl-2,3-beta-galactosyl-1,3)-N-acetylgalactosaminide alpha-2,6-sialyltransferase 1 |
| 17 | 72173649 | rs9897045 | xxx | 0.0000495 | IgG | LEVEL | 55808 | ST6GALNAC1 | ST6 (alpha-N-acetyl-neuraminyl-2,3-beta-galactosyl-1,3)-N-acetylgalactosaminide alpha-2,6-sialyltransferase 1 |
| 18 | 4012527 | rs4798157 | xxx | 0.000024 | IgG | PRESENCE ABSENCE | 388458 | LOC388458 | hypothetical gene supported by BC040718 |
| 18 | 4015719 | rs1442385 | xxx | 0.000019 | IgG | PRESENCE ABSENCE | 388458 | LOC388458 | hypothetical gene supported by BC040718 |
| 18 | 4016587 | rs1372631 | xxx | 0.00004197 | ASCA | PRESENCE ABSENCE | 388458 | LOC388458 | hypothetical gene supported by BC040718 |

FIG. 10Q

| | | | | | | | |
|---|---|---|---|---|---|---|---|
| 18 | 4016587 | rs1372631 | xxx | 0.00006557 | IgA | LEVEL | | 388458 | LOC388458 | hypothetical gene supported by BC040718 |
| 18 | 4016587 | rs1372631 | xxxxxx | 0.000001 | IgG | PRESENCE ABSENCE | | 388458 | LOC388458 | hypothetical gene supported by BC040718 |
| 18 | 4016587 | rs1372631 | xxx | 0.000028 | IgG | LEVEL | LOGARITHMIC | 388458 | LOC388458 | hypothetical gene supported by BC040718 |
| 18 | 8872679 | rs8094017 | xxx | 0.000021 | ASCA | PRESENCE ABSENCE | | 23255 | KIAA0802 | KIAA0802 |
| 18 | 8872679 | rs8094017 | xxx | 0.0000616 | IgG | PRESENCE ABSENCE | | 23255 | KIAA0802 | KIAA0802 |
| 18 | 8872679 | rs8094017 | xxx | 0.000036 | IgG | LEVEL | LOGARITHMIC | 23255 | KIAA0802 | KIAA0802 |
| 18 | 11807585 | rs12454673 | xxx | 0.00004082 | IgG | LEVEL | LOGARITHMIC | 2774 | GNAL | guanine nucleotide binding protein (G protein), alpha activating activity polypeptide, olfactory type |
| 18 | 20752168 | rs1786153 | xxx | 0.00007105 | anti-i2 | PRESENCE ABSENCE | | 25925 | ZNF521 | zinc finger protein 521 |
| 18 | 51958209 | rs1789588 | xxx | 0.000028 | anti-i2 | PRESENCE ABSENCE | | 642484 | FLJ45743 | hypothetical protein LOC642484 |
| 18 | 63184658 | rs9951011 | xxx | 0.00006993 | IgA | LEVEL | | 92126 | DSEL | dermatan sulfate epimerase-like |
| 18 | 63300140 | rs1061568 | xxx | 0.00005764 | ALL | SUM | ADJUSTED | 92126 | DSEL | dermatan sulfate epimerase-like |
| 18 | 63483660 | rs7244904 | xxx | 0.00006345 | IgG | LEVEL | LOGARITHMIC | 92126 | DSEL | dermatan sulfate epimerase-like |
| 18 | 65301877 | rs1036837 | xxx | 0.00009153 | anti-i2 | PRESENCE ABSENCE | | 220164 | DOK6 | docking protein 6 |
| 18 | 65301877 | rs1036837 | xxx | 0.00006067 | ALL | SUM | ADJUSTED | 220164 | DOK6 | docking protein 6 |
| 19 | 2872008 | rs8108501 | xxx | 0.000027 | IgA | LEVEL | | 58492 | ZNF77 | zinc finger protein 77 |
| 19 | 2884480 | rs3786948 | xxx | 0.00008677 | IgA | LEVEL | | 58492 | ZNF77 | zinc finger protein 77 |

FIG. 10R

| | | | | | | |
|---|---|---|---|---|---|---|
| 19 | 3055629 | rs308052 | xxx | 0.0000551 | ASCA | PRESENCE ABSENCE | | |
| 19 | 17887794 | rs4808716 | xxx | 0.00006844 | IgA | PRESENCE ABSENCE | | |
| 19 | 19164802 | rs1050483 | xxx | 0.000021 | IgA | LEVEL | | |
| 19 | 19196083 | rs2238672 | xxx | 0.00004772 | IgA | PRESENCE ABSENCE | | |
| 19 | 19196083 | rs2238672 | xxx | 0.00006542 | IgA | LEVEL | | |
| 19 | 34854335 | rs10424881 | xxx | 0.00009732 | anti-CBir1 | PRESENCE ABSENCE | 79156 | PLEKHF1 | pleckstrin homology domain containing, family F (with FYVE domain) member 1 |
| 19 | 35631829 | rs33431 | xxx | 0.00004032 | ASCA | PRESENCE ABSENCE | 9745 | ZNF536 | zinc finger protein 536 |
| 19 | 45141888 | rs2231738 | xxx | 0.00004603 | IgA | LEVEL | 5704 | PSMC4 | proteasome (prosome, macropain) 26S subunit, ATPase, 4 |
| 19 | 45169305 | rs234370 | xxx | 0.00007812 | IgA | LEVEL | 5704 | PSMC4 | proteasome (prosome, macropain) 26S subunit, ATPase, 4 |
| 19 | 45172763 | rs371500 | xxx | 0.00005261 | IgA | LEVEL | 5704 | PSMC4 | proteasome (prosome, macropain) 26S subunit, ATPase, 4 |
| 19 | 45181310 | rs8105066 | xxx | 0.00006768 | IgA | LEVEL | 5704 | PSMC4 | proteasome (prosome, macropain) 26S subunit, ATPase, 4 |
| 19 | 46253015 | rs459091 | xxx | 0.000028 | IgA | LEVEL | | ZNF780B | |
| 19 | 57313456 | rs81111640 | xxx | 0.0000789 | anti-I2 | PRESENCE ABSENCE | 90317 | ZNF616 | zinc finger protein 616 |

Note: Rows 1–2 map to GNA11 (2767, "guanine nucleotide binding protein (G protein), alpha 11 (Gq class)") and CCDC124 (115098, "coiled-coil domain containing 124"); row 3 to RFXANK (8625, "regulatory factor X-associated ankyrin-containing protein"); rows 4–5 to NCAN (1463, "neurocan").

FIG. 10S

| | | | | | | | | | |
|---|---|---|---|---|---|---|---|---|---|
| 19 | 62414825 | rs917340 | xxx | 0.00005952 | IgG | LEVEL | LOGARITHMIC | 9422 | ZNF264 | zinc finger protein 264 |
| 20 | 12937901 | rs3761896 | xxx | 0.000017 | anti-OMPC | LEVEL | | 55304 | SPTLC3 | serine palmitoyltransferase, long chain base subunit 3 |
| 20 | 14748958 | rs6034046 | xxx | 0.000011 | anti-OMPC | LEVEL | | 140733 | C20orf133 | chromosome 20 open reading frame 133 |
| 20 | 17411917 | rs6044842 | xxx | 0.00008138 | ASCA | PRESENCE ABSENCE | | 5126 | PCSK2 | proprotein convertase subtilisin/kexin type 2 |
| 20 | 21729363 | rs6047633 | xxxxx | 0.000006 | ASCA | PRESENCE ABSENCE | | 5075 | PAX1 | paired box gene 1 |
| 20 | 21729363 | rs6047633 | xxxxx | 0.000006 | IgG | PRESENCE ABSENCE | | 5075 | PAX1 | paired box gene 1 |
| 20 | 21729363 | rs6047633 | xxx | 0.00003 | IgG | LEVEL | LOGARITHMIC | 5075 | PAX1 | paired box gene 1 |
| 20 | 21733073 | rs6047637 | xxx | 0.00006768 | ASCA | PRESENCE ABSENCE | | 5075 | PAX1 | paired box gene 1 |
| 20 | 21897593 | rs6106434 | xxx | 0.00006417 | ASCA | PRESENCE ABSENCE | | 5075 | PAX1 | paired box gene 1 |
| 20 | 52435022 | rs6023181 | xxx | 0.000017 | ASCA | PRESENCE ABSENCE | | 55816 | DOK5 | docking protein 5 |
| 20 | 52435022 | rs6023181 | xxxxx | 0.000008 | IgG | PRESENCE ABSENCE | | 55816 | DOK5 | docking protein 5 |
| 20 | 52435022 | rs6023181 | xxxxx | 0.000003 | IgG | LEVEL | LOGARITHMIC | 55816 | DOK5 | docking protein 5 |
| 20 | 52435022 | rs6023181 | xxx | 0.000018 | IgG | LEVEL | | 55816 | DOK5 | docking protein 5 |
| 20 | 52470314 | rs6023227 | xxxxx | 0.000004 | ASCA | PRESENCE ABSENCE | | 55816 | DOK5 | docking protein 5 |
| 20 | 52470314 | rs6023227 | xxx | 0.00005764 | IgA | LEVEL | | 55816 | DOK5 | docking protein 5 |
| 20 | 52470314 | rs6023227 | xxx | 0.000033 | IgG | PRESENCE ABSENCE | | 55816 | DOK5 | docking protein 5 |
| 20 | 52470314 | rs6023227 | xxx | 0.000021 | IgG | LEVEL | | 55816 | DOK5 | docking protein 5 |
| 20 | 52470314 | rs6023227 | xxx | 0.000017 | IgG | LEVEL | LOGARITHMIC | 55816 | DOK5 | docking protein 5 |

FIG. 10T

| | | | | | | | |
|---|---|---|---|---|---|---|---|
| 20 | 56807638 | rs6100226 | xxx | 0.00004866 | IgA | LEVEL SUM | 2778 | GNAS | GNAS complex locus |
| 20 | 56807638 | rs6100226 | xxx | 0.00004525 | ALL | QUARTILE | 2778 | GNAS | GNAS complex locus |
| 20 | 59971956 | rs6061396 | xxx | 0.000013 | anti-OMPC | PRESENCE ABSENCE | 6874 | TAF4 | TAF4 RNA polymerase II, TATA box binding protein (TBP)-associated factor, 135kDa |
| 20 | 59997019 | rs6089583 | xxx | 0.00006868 | anti-OMPC | PRESENCE ABSENCE | 6874 | TAF4 | TAF4 RNA polymerase II, TATA box binding protein (TBP)-associated factor, 135kDa |
| 20 | 33454426 | rs2834115 | xxx | 0.000021 | anti-OMPC | PRESENCE ABSENCE | | BC105117 | |
| 21 | 33539959 | rs2834159 | xxx | 0.00005556 | anti-CBir1 | PRESENCE ABSENCE | 3455 | IFNAR2 | interferon (alpha, beta and omega) receptor 2 |
| 21 | 22476629 | rs9620326 | xxx | 0.0000554 | IgG | LEVEL | 6598 | SMARCB1 | SWI/SNF related, matrix associated, actin dependent regulator of chromatin, subfamily b, member 1 |
| 22 | 34773651 | rs6000083 | xxx | 0.00008819 | IgG | PRESENCE ABSENCE | 23543 | RBM9 | RNA binding motif protein 9 |
| 22 | 370062770 | rs13054361 | xxx | 0.000022 | IgA | PRESENCE ABSENCE | 730115 | LOC730115 | hypothetical protein LOC730115 |
| 22 | 370062770 | rs13054361 | xxx | 0.00005208 | ALL | SUM QUARTILE | 730115 | LOC730115 | hypothetical protein LOC730115 |
| 22 | 46585519 | rs10854841 | xxx | 0.00005548 | ALL | SUM QUARTILE | | FLJ35788 | |

FIG. 11A

| No | CHR | SNP | A1 | F_A | F_U | A2 | CHISQ | P | OR | Location | Gene Name | Comments |
|---|---|---|---|---|---|---|---|---|---|---|---|---|
| 174 | 12 | rs2682292 | C | 0.3796 | 0.4363 | A | 7.08 | 0.007805 | 0.7904 | 51626209 | KRT8/KRT18 | keratin 8 & keratin 18 |
| 93 | 6 | rs367398 | A | 0.3864 | 0.3337 | G | 6.57 | 0.01039 | 1.257 | 32299708 | Chr6 Mapping | Notch 4 |
| 173 | 12 | rs12423065 | A | 0.3821 | 0.4358 | G | 6.39 | 0.01147 | 0.8008 | 51625301 | KRT8/KRT18 | keratin 8 & keratin 18 |
| 97 | 6 | rs9296012 | A | 0.208 | 0.167 | G | 6.18 | 0.0129 | 1.31 | 32303310 | Chr6 Mapping | Notch 4 |
| 229 | 14 | rs4982753 | A | 0.3062 | 0.2594 | G | 5.98 | 0.01451 | 1.26 | 22884409 | Chr14 Mapping | solute carrier family 22 (organic cation) |
| 159 | 12 | rs2853564 | G | 0.4264 | 0.3754 | A | 5.91 | 0.01509 | 1.237 | 46564754 | VDR | vitamin D receptor |
| 168 | 12 | rs12580050 | T | 0.3463 | 0.3966 | A | 5.8 | 0.01601 | 0.806 | 51586470 | KRT8/KRT18 | keratin 8 & keratin 18 |
| 176 | 12 | rs2070876 | A | 0.354 | 0.4037 | G | 5.62 | 0.01775 | 0.8096 | 51631097 | KRT8/KRT18 | keratin 8 & keratin 18 |
| 252 | 14 | rs178634 | G | 0.1062 | 0.07839 | C | 5.27 | 0.02173 | 1.397 | 22919839 | CMTM5 | chemokine-like factor superfamily 5 isoform a |
| 214 | 14 | rs2025210 | A | 0.1202 | 0.1539 | C | 5.02 | 0.02505 | 0.7506 | 22333978 | SLC7A7 | solute carrier family 7 (cationic acid) |
| 215 | 14 | rs5027249 | G | 0.1757 | 0.214 | A | 4.93 | 0.02637 | 0.7827 | 22340436 | SLC7A7 | solute carrier family 7 (cationic acid) |
| 172 | 12 | rs2172276 | G | 0.3523 | 0.3982 | A | 4.82 | 0.0282 | 0.822 | 51624308 | KRT8/KRT18 | keratin 8 & keratin 18 |
| 78 | 5 | rs2853694 | C | 0.4276 | 0.474 | A | 4.68 | 0.0305 | 0.8292 | 158681666 | IL12B | interleukin 12 beta |
| 141 | 12 | rs1461567 | A | 0.2687 | 0.3104 | G | 4.5 | 0.03389 | 0.8164 | 42450956 | IRAK4 | interleukin-1 receptor-associated kinase 4 |
| 246 | 14 | rs11465506 | A | 0.0065 | 0.01674 | G | 4.17 | 0.04108 | 0.3849 | 22912501 | IL25 | interleukin 25 |
| 269 | 14 | rs10146843 | C | 0.3805 | 0.3391 | G | 4.07 | 0.04374 | 1.197 | 23472852 | Chr14 Mapping | C14orf165 |
| 157 | 12 | rs2254210 | A | 0.3769 | 0.3357 | G | 4.05 | 0.04418 | 1.197 | 46559981 | VDR | vitamin D receptor |
| 31 | 1 | rs1569922 | A | 0.3057 | 0.3462 | G | 4 | 0.0456 | 0.8314 | 67376984 | IL23R | interleukin 23 receptor |
| 129 | 10 | rs570613 | G | 0.3385 | 0.3794 | A | 3.91 | 0.04814 | 0.8369 | 8146508 | GATA3 | GATA binding protein 3 isoform 1 |
| 106 | 6 | rs7747909 | A | 0.2571 | 0.222 | G | 3.73 | 0.05334 | 1.213 | 52162208 | IL17 | |
| 289 | 19 | rs5030390 | A | 0.0687 | 0.09177 | A | 3.72 | 0.05384 | 0.7295 | 10243537 | ICAM1 | |
| 46 | 3 | rs11919639 | C | 0.0452 | 0.06416 | A | 3.53 | 0.06024 | 0.6908 | 113691440 | BTLA | Questionable but WORK |
| 142 | 12 | rs4251501 | C | 0.0116 | 0.02268 | A | 3.48 | 0.06195 | 0.507 | 42457911 | IRAK4 | Questionable but WORK |
| 300 | 21 | rs2284553 | A | 0.3536 | 0.3926 | G | 3.48 | 0.06212 | 0.8465 | 33698565 | IFNGR2 | |
| 15 | 1 | rs2229579 | A | 0.1266 | 0.1019 | G | 3.4 | 0.06503 | 1.278 | 23946468 | CNR2 | |
| 283 | 19 | rs2279627 | G | 0.2158 | 0.2494 | C | 3.38 | 0.06608 | 0.8278 | 6614594 | TNFSF14 (LIGHT) | |
| 213 | 14 | rs8006372 | G | 0.4044 | 0.3673 | A | 3.18 | 0.07465 | 1.17 | 22329539 | Chr14 Mapping | |
| 165 | 12 | rs4351899 | A | 0.5247 | 0.4872 | C | 3.03 | 0.08176 | 1.162 | 51581088 | KRT8/KRT18 | |

FIG. 11B

| | | | | | | | | | |
|---|---|---|---|---|---|---|---|---|---|
| 105 | 6 | rs10484879 | A | 0.2532 | 0.2218 | C | 3.01 | 0.08257 | 1.19 | 52159916 | IL17 |
| 167 | 12 | rs2035875 | A | 0.5233 | 0.4861 | G | 2.99 | 0.08385 | 1.16 | 51582184 | KRT8/KRT18 |
| 37 | 1 | rs2201841 | G | 0.4028 | 0.3671 | A | 2.94 | 0.08648 | 1.163 | 67406223 | IL23R |
| 85 | 6 | rs2854050 | A | 0.0788 | 0.1001 | G | 2.9 | 0.08888 | 0.769 | 32293583 | Chr6 Mapping | Questionable but WORK |
| 74 | 4 | rs3774968 | A | 0.474 | 0.4378 | G | 2.87 | 0.09055 | 1.157 | 103888305 | NFKB1 |
| 137 | 12 | rs2078178 | A | 0.2248 | 0.2561 | G | 2.85 | 0.0912 | 0.8424 | 101167829 | CLEC7A (Dectin) |
| 45 | 3 | rs2705534 | C | 0.0827 | 0.104 | A | 2.79 | 0.09482 | 0.7767 | 113691075 | BTLA |
| 158 | 12 | rs2238136 | A | 0.239 | 0.2705 | G | 2.78 | 0.09554 | 0.8472 | 46563980 | VDR |

FIG. 12A

| CHR | SNP | A1 | F_A | F_U | A2 | CHISQ | P | OR | Location | Gene Name | Comments |
|---|---|---|---|---|---|---|---|---|---|---|---|
| 6 | rs415929 | G | 0.4236 | 0.3634 | A | 8.307 | 0.00395 | 1.287 | 32297010 | Chr6 Mapping | Notch 4 |
| 1 | rs2863212 | G | 0.06865 | 0.1039 | A | 7.93 | 0.00486 | 0.636 | 67397137 | IL23R | Interleukin 23 receptor |
| 6 | rs367398 | A | 0.3877 | 0.3331 | G | 7.039 | 0.00798 | 1.268 | 32299708 | Chr6 Mapping | Notch 4 |
| 14 | rs178634 | G | 0.107 | 0.0781 | C | 5.665 | 0.01731 | 1.415 | 22919839 | CMTM5 | chemokine-like factor superfamily 5 isoform a |
| 12 | rs2853564 | G | 0.4249 | 0.3761 | A | 5.404 | 0.02009 | 1.225 | 46564754 | VDR | vitamin D receptor |
| 12 | rs7298416 | A | 0.1218 | 0.1564 | G | 5.193 | 0.02267 | 0.748 | 10177251 | CLEC7A (Dectin) | dendritic cell-associated C-type lectin 1 |
| 14 | rs12889813 | A | 0.285 | 0.2425 | G | 5.126 | 0.02357 | 1.245 | 23376377 | Chr14 Mapping | C14orf165 |
| 12 | rs10783219 | T | 0.3109 | 0.3558 | A | 4.85 | 0.02765 | 0.817 | 46581755 | VDR | vitamin D receptor |
| 19 | rs2306190 | C | 0.3744 | 0.4203 | G | 4.725 | 0.02972 | 0.825 | 14023676 | IL27RA | Interleukin 23 receptor alpha subunit |
| 12 | rs2254210 | A | 0.3792 | 0.3348 | G | 4.696 | 0.03023 | 1.214 | 46559981 | VDR | vitamin D receptor |
| 6 | rs6907458 | A | 0.07772 | 0.0556 | G | 4.533 | 0.03325 | 1.433 | 32279266 | Chr6 Mapping | Notch 4 |
| 4 | rs2227306 | A | 0.364 | 0.4087 | G | 4.532 | 0.03327 | 0.828 | 74972090 | IL8 | interleukin 8 |
| 12 | rs11053624 | G | 0.07143 | 0.0969 | A | 4.307 | 0.03795 | 0.717 | 10174978 | CLEC7A (Dectin) | dendritic cell-associated C-type lectin 1 |
| 22 | rs721930 | G | 0.2318 | 0.1971 | C | 3.935 | 0.0473 | 1.229 | 15960362 | IL17R | interleukin 17 receptor |
| 6 | rs9296012 | A | 0.2021 | 0.1696 | G | 3.875 | 0.04902 | 1.24 | 32303310 | Chr6 Mapping | Notch 4 |
| 4 | rs11730667 | G | 0.4054 | 0.447 | A | 3.797 | 0.05134 | 0.844 | 74965246 | IL8 | |
| 22 | rs2041629 | A | 0.1995 | 0.168 | G | 3.686 | 0.05487 | 1.234 | 15931698 | IL17R | |
| 12 | rs2238136 | A | 0.2358 | 0.2718 | G | 3.65 | 0.05605 | 0.826 | 46563980 | VDR | |
| 4 | rs2227307 | C | 0.3964 | 0.4369 | A | 3.645 | 0.05624 | 0.846 | 74971704 | IL8 | |
| 14 | rs178633 | C | 0.03368 | 0.021 | G | 3.602 | 0.05771 | 1.625 | 22907989 | Chr14 Mapping | |
| 14 | rs6572754 | A | 0.2085 | 0.2428 | G | 3.558 | 0.05926 | 0.822 | 22327900 | Chr14 Mapping | |
| 6 | rs7747909 | A | 0.2565 | 0.2223 | G | 3.531 | 0.06022 | 1.206 | 52162208 | IL17 | |
| 6 | rs9267845 | T | 0.4547 | 0.4147 | A | 3.526 | 0.06042 | 1.177 | 32301676 | Chr6 Mapping | |
| 21 | rs2284553 | A | 0.3536 | 0.3926 | G | 3.48 | 0.06212 | 0.847 | 33698565 | IFNGR2 | |
| 22 | rs2241049 | G | 0.386 | 0.3476 | A | 3.473 | 0.06238 | 1.18 | 15962234 | IL17R | |
| 4 | rs4694637 | G | 0.4016 | 0.4408 | A | 3.392 | 0.0655 | 0.851 | 74977869 | IL8 | |
| 6 | rs9267853 | A | 0.2448 | 0.2799 | G | 3.377 | 0.06613 | 0.834 | 32303229 | Chr6 Mapping | |

FIG. 12B

| | | | | | | | | | | |
|---|---|---|---|---|---|---|---|---|---|---|
| 22 | rs9606603 | A | 0.4896 | 0.4508 | T | 3.287 | 0.06983 | 1.169 | 15936067 | IL17R |
| 4 | rs4694178 | C | 0.4016 | 0.4392 | A | 3.137 | 0.07652 | 0.857 | 74977723 | IL8 |
| 19 | rs2277984 | A | 0.4663 | 0.5039 | G | 3.052 | 0.08062 | 0.86 | 6630511 | TNFSF14 (LIGHT) |

FIG. 13A

| No | CHR | SNP | A1 | F_A | F_U | A2 | CHISQ | P | OR | Location | Gene Name | Comments |
|---|---|---|---|---|---|---|---|---|---|---|---|---|
| 15 | 1 | rs2229579 | A | 0.133 | 0.09944 | G | 6.287 | 0.01216 | 1.389 | 23946468 | CNR2 | Cannabinoid receptor 2 (macrophage) |
| 19 | 1 | rs16828926 | A | 0.188 | 0.1454 | G | 7.423 | 0.006439 | 1.361 | 23960436 | CNR2 | Cannabinoid receptor 2 (macrophage) |
| 20 | 1 | rs2501390 | A | 0.1905 | 0.1467 | G | 7.809 | 0.0052 | 1.37 | 23961102 | CNR2 | Cannabinoid receptor 2 (macrophage) |
| 21 | 1 | rs2502959 | A | 0.1931 | 0.1548 | C | 5.757 | 0.01642 | 1.306 | 23962167 | CNR2 | Cannabinoid receptor 2 (macrophage) |
| 22 | 1 | rs2502965 | G | 0.1905 | 0.1471 | A | 7.662 | 0.00564 | 1.365 | 23963582 | CNR2 | Cannabinoid receptor 2 (macrophage) |
| 93 | 6 | rs367398 | A | 0.3827 | 0.3352 | G | 5.38 | 0.02037 | 1.23 | 32299708 | Chr6 Mapping | Notch 4 |
| 95 | 6 | rs9267845 | T | 0.4629 | 0.4121 | A | 5.744 | 0.01654 | 1.229 | 32301676 | Chr6 Mapping | Notch 4 |
| 97 | 6 | rs9296012 | A | 0.2174 | 0.1632 | G | 10.89 | 0.0009669 | 1.425 | 32303310 | Chr6 Mapping | Notch 4 |
| 141 | 12 | rs1461567 | A | 0.257 | 0.3165 | G | 9.193 | 0.00243 | 0.7472 | 42450956 | IRAK4 | interleukin-1 receptor-associated kinase 4 |
| 203 | 14 | rs8013531 | A | 0.4038 | 0.4544 | G | 5.657 | 0.01739 | 0.8132 | 22317527 | SLC7A7 | solute carrier family 7 (cationic amino acid) |
| 258 | 14 | rs12435647 | A | 0.1394 | 0.1809 | G | 6.716 | 0.009554 | 0.7333 | 23379705 | Chr14 Mapping | C14orf165 |
| 290 | 19 | rs281432 | C | 0.455 | 0.5039 | G | 5.193 | 0.02268 | 0.822 | 10251658 | ICAM1 | intercellular adhesion molecule 1 |
| 307 | 22 | rs2241042 | A | 0.4118 | 0.3667 | C | 4.705 | 0.03008 | 1.209 | 15942253 | IL17R | interleukin 17 receptor |
| 6 | 1 | rs3007421 | A | 0.1113 | 0.1428 | G | 4.692 | 0.03031 | 0.7516 | 6464455 | TNFRSF25 (DR3) | tumor necrosis factor receptor superfamily |
| 194 | 14 | rs7785 | A | 0.06905 | 0.04828 | A | 4.562 | 0.03269 | 1.462 | 20014854 | Chr14 Mapping | NP-purine nucleoside phosphorylase |
| 128 | 10 | rs1399180 | A | 0.1195 | 0.1513 | G | 4.507 | 0.03375 | 0.7613 | 8138725 | GATA3 | GATA binding protein 3 isoform 1 |
| 216 | 14 | rs12884337 | A | 0.3299 | 0.3733 | A | 4.458 | 0.03474 | 0.8265 | 22342954 | SLC7A7 | solute carrier family 7 (cationic amino acid) |
| 130 | 10 | rs528778 | A | 0.1471 | 0.1809 | A | 4.415 | 0.03562 | 0.7806 | 8152149 | GATA3 | GATA binding protein 3 isoform 1 |
| 213 | 14 | rs8006372 | G | 0.3491 | 0.3918 | A | 4.222 | 0.03991 | 0.8326 | 22329539 | SLC7A7 | solute carrier family 7 (cationic amino acid) |
| 4 | 1 | rs2986754 | C | 0.06795 | 0.09232 | A | 4.158 | 0.04143 | 0.7167 | 6460731 | TNFRSF25 (DR3) | tumor necrosis factor receptor superfamily |
| 7 | 1 | rs2986753 | G | 0.1121 | 0.1413 | A | 4.023 | 0.04488 | 0.7671 | 6464701 | TNFRSF25 (DR3) | tumor necrosis factor receptor superfamily |
| 244 | 14 | rs101149449 | G | 0.08312 | 0.1088 | A | 3.951 | 0.04685 | 0.7428 | 22910351 | IL25 | interleukin 25 |
| 42 | 3 | rs1982809 | G | 0.2046 | 0.24 | A | 3.865 | 0.0493 | 0.8146 | 113665430 | BTLA | B and T lymphocyte associated |
| 44 | 3 | rs9288953 | A | 0.2877 | 0.3267 | G | 3.832 | 0.05027 | 0.8326 | 113685942 | BTLA | B and T lymphocyte associated |
| 46 | 3 | rs11919639 | C | 0.04476 | 0.06437 | A | 3.814 | 0.05083 | 0.681 | 113691440 | BTLA | B and T lymphocyte associated |
| 41 | 1 | rs1343151 | A | 0.2596 | 0.2952 | G | 3.403 | 0.06509 | 0.837 | 67431150 | IL23R | |
| 190 | 14 | rs17713460 | G | 0.3141 | 0.2786 | A | 3.341 | 0.06757 | 1.186 | 20003455 | Chr14 Mapping | |
| 80 | 6 | rs6907458 | A | 0.07584 | 0.05681 | G | 3.34 | 0.06761 | 1.362 | 32279266 | Chr6 Mapping | |

FIG. 13B

| | | | | | | | | | |
|---|---|---|---|---|---|---|---|---|---|
| 78 | 5 | rs2853694 | C | 0.4335 | 0.4722 | A | 3.29 | 0.06972 | 0.8553 | 158681666 | IL12B | |
| 5 | 1 | rs3007420 | G | 0.05256 | 0.07183 | C | 3.274 | 0.07041 | 0.7169 | 6464089 | TNFRSF25 (DR3) | |
| 118 | 9 | rs7847158 | G | 0.2295 | 0.2628 | A | 3.197 | 0.07378 | 0.8355 | 114639819 | TNFSF15 (TL1A) | Questionable but WORK |
| 31 | 1 | rs1569922 | A | 0.309 | 0.3446 | G | 3.11 | 0.07783 | 0.8503 | 67376984 | IL23R | |
| 90 | 6 | rs915895 | A | 0.2059 | 0.2375 | G | 3.101 | 0.07827 | 0.8323 | 32298195 | Chr6 Mapping | Questionable but WORK |
| 91 | 6 | rs443198 | G | 0.4284 | 0.3917 | A | 3.056 | 0.08043 | 1.164 | 32298384 | Chr6 Mapping | |
| 96 | 6 | rs9267853 | A | 0.2455 | 0.2783 | G | 2.989 | 0.08386 | 0.8438 | 32303229 | Chr6 Mapping | |
| 37 | 1 | rs2201841 | G | 0.4026 | 0.3667 | A | 2.984 | 0.08409 | 1.164 | 67406223 | IL23R | |

FIG. 14

| CHR | SNP | A1 | F_A | F_U | A2 | CHISQ | P | OR | Location | Gene Name | Comments |
|---|---|---|---|---|---|---|---|---|---|---|---|
| 6 | rs9296012 | A | 0.2008 | 0.1581 | G | 7.983 | 0.004721 | 1.338 | 32303310 | Chr6 Mapping | Notch 4 |
| 22 | rs2241042 | A | 0.4068 | 0.3536 | C | 7.751 | 0.005369 | 1.254 | 15942253 | IL17R | interleukin 17 receptor |
| 12 | rs1461567 | A | 0.275 | 0.3222 | G | 6.838 | 0.008925 | 0.7983 | 42450956 | IRAK4 | interleukin-1 receptor-associated kinase 4 |
| 10 | rs528778 | A | 0.1523 | 0.1893 | G | 6.229 | 0.01256 | 0.7697 | 8152149 | GATA3 | GATA binding protein 3 isoform 1 |
| 22 | rs9606603 | A | 0.4854 | 0.4393 | T | 5.521 | 0.01879 | 1.204 | 15936067 | IL17R | interleukin 17 receptor |
| 22 | rs882643 | C | 0.1162 | 0.1456 | G | 4.939 | 0.02625 | 0.7709 | 15966377 | IL17R | interleukin 17 receptor |
| 1 | rs11209008 | A | 0.01923 | 0.03271 | G | 4.647 | 0.0311 | 0.5798 | 67335319 | IL23R | interleukin 23 receptor |
| 10 | rs1399180 | A | 0.1269 | 0.1565 | G | 4.598 | 0.03201 | 0.7837 | 8138725 | GATA3 | GATA binding protein 3 isoform 1 |
| 12 | rs3858733 | C | 0.03769 | 0.0234 | A | 4.445 | 0.03501 | 1.635 | 46524234 | VDR | vitamin D receptor |
| 9 | rs7847158 | G | 0.2349 | 0.2707 | A | 4.356 | 0.03688 | 0.8274 | 114639819 | TNFSF15 (TL1A) | tl1a |
| 3 | rs2705534 | C | 0.08538 | 0.109 | A | 4.12 | 0.04239 | 0.7628 | 136911075 | BTLA | B and T lymphocyte associated |
| 4 | rs2227306 | A | 0.3775 | 0.4159 | G | 3.974 | 0.04621 | 0.8517 | 74972090 | IL8 | interleukin 8 |
| 3 | rs2633582 | C | 0.08538 | 0.1083 | A | 3.867 | 0.04926 | 0.769 | 113702030 | BTLA | B and T lymphocyte associated |
| 21 | rs9808753 | G | 0.1523 | 0.1262 | A | 3.681 | 0.05504 | 1.244 | 33709182 | IFNGR2 | |
| 19 | rs8106574 | A | 0.2092 | 0.2407 | G | 3.66 | 0.05574 | 0.8349 | 6622142 | TNFSF14 (LIGHT) | |
| 10 | rs1244186 | A | 0.2231 | 0.2547 | G | 3.548 | 0.05962 | 0.8403 | 8132689 | GATA3 | |
| 1 | rs2986751 | A | 0.06857 | 0.08814 | G | 3.425 | 0.06421 | 0.7616 | 6469047 | TNFRSF25 (DR3) | |
| 1 | rs2986754 | C | 0.07538 | 0.09468 | G | 3.086 | 0.07895 | 0.7796 | 6460731 | TNFRSF25 (DR3) | |
| 14 | rs8017550 | G | 0.05932 | 0.04439 | C | 2.924 | 0.08727 | 1.358 | 22910159 | Chr14 Mapping | |
| 21 | rs11088251 | C | 0.1477 | 0.1248 | A | 2.872 | 0.09015 | 1.215 | 33692680 | IFNGR2 | |
| 6 | rs6907458 | A | 0.07043 | 0.05459 | G | 2.734 | 0.09826 | 1.312 | 32279266 | Chr6 Mapping | |
| 1 | rs3007420 | G | 0.05796 | 0.0741 | C | 2.723 | 0.09893 | 0.7687 | 6464089 | TNFRSF25 (DR3) | |
| 1 | rs3007421 | A | 0.1223 | 0.1443 | G | 2.705 | 0.1 | 0.8263 | 6464455 | TNFRSF25 (DR3) | |

FIG. 15A

| CHR | SNP | A1 | F_A | F_U | A2 | CHISQ | P | OR | Location | Gene Name | Comments |
|---|---|---|---|---|---|---|---|---|---|---|---|
| 6 | rs415929 | G | 0.4236 | 0.3634 | A | 8.307 | 0.003949 | 1.287 | 32297010 | Chr6 Mapping | Notch 4 |
| 1 | rs2863212 | G | 0.06865 | 0.1039 | A | 7.93 | 0.004862 | 0.636 | 67397137 | IL23R | interleukin 23 receptor |
| 6 | rs367398 | A | 0.3877 | 0.3331 | G | 7.039 | 0.007976 | 1.268 | 32299708 | Chr6 Mapping | Notch 4 |
| 14 | rs178634 | G | 0.107 | 0.07813 | C | 5.665 | 0.01731 | 1.415 | 22919839 | CMTM5 | chemokine-like factor superfamily 5 isoform a |
| 12 | rs2853564 | G | 0.4249 | 0.3761 | A | 5.404 | 0.02009 | 1.225 | 46564754 | VDR | vitamin D receptor |
| 12 | rs7298416 | A | 0.1218 | 0.1564 | G | 5.193 | 0.02267 | 0.7481 | 10177251 | CLEC7A (Dectin) | dendritic cell-associated C-type lectin 1 |
| 14 | rs12889813 | A | 0.285 | 0.2425 | G | 5.126 | 0.02357 | 1.245 | 23376377 | Chr14 Mapping | unknown gene |
| 12 | rs10783219 | T | 0.3109 | 0.3558 | A | 4.85 | 0.02765 | 0.8168 | 46581755 | VDR | vitamin D receptor |
| 19 | rs2306190 | C | 0.3744 | 0.4203 | A | 4.725 | 0.02972 | 0.8254 | 14023676 | IL27RA | interleukin 27 receptor |
| 12 | rs2254210 | A | 0.3792 | 0.3348 | G | 4.696 | 0.03023 | 1.214 | 46559981 | VDR | vitamin D receptor |
| 6 | rs6907458 | A | 0.07772 | 0.05556 | G | 4.533 | 0.03325 | 1.433 | 32279266 | Chr6 Mapping | Notch 4 |
| 4 | rs2227306 | A | 0.364 | 0.4087 | G | 4.532 | 0.03327 | 0.8279 | 74972090 | IL8 | interleukin 8 |
| 12 | rs11053624 | G | 0.07143 | 0.0969 | A | 4.307 | 0.03795 | 0.7169 | 10174978 | CLEC7A (Dectin) | dendritic cell-associated C-type lectin 1 |
| 22 | rs721930 | G | 0.2318 | 0.1971 | C | 3.935 | 0.0473 | 1.229 | 15960362 | IL17R | interleukin 17 receptor |
| 6 | rs9296012 | A | 0.2021 | 0.1696 | G | 3.875 | 0.04902 | 1.24 | 32303310 | Chr6 Mapping | Notch 4 |
| 4 | rs117730667 | G | 0.4054 | 0.447 | A | 3.797 | 0.05134 | 0.8438 | 74965246 | IL8 | |
| 22 | rs2041629 | A | 0.1995 | 0.168 | G | 3.686 | 0.05487 | 1.234 | 15931698 | IL17R | |
| 12 | rs2238136 | A | 0.2358 | 0.2718 | G | 3.65 | 0.05605 | 0.8264 | 46563980 | VDR | |
| 4 | rs2227307 | C | 0.3964 | 0.4369 | A | 3.645 | 0.05624 | 0.8462 | 74971704 | IL8 | |
| 14 | rs178633 | C | 0.03368 | 0.02099 | G | 3.602 | 0.05771 | 1.625 | 22907989 | Chr14 Mapping | |
| 14 | rs6572754 | A | 0.2085 | 0.2428 | G | 3.558 | 0.05926 | 0.8217 | 22327900 | Chr14 Mapping | |
| 6 | rs7747909 | A | 0.2565 | 0.2223 | G | 3.531 | 0.06022 | 1.206 | 52162208 | IL17 | |
| 6 | rs9267845 | T | 0.4547 | 0.4147 | A | 3.526 | 0.06042 | 1.177 | 32301676 | Chr6 Mapping | |
| 21 | rs2284553 | A | 0.3536 | 0.3926 | G | 3.48 | 0.06212 | 0.8465 | 33698565 | IFNGR2 | |
| 22 | rs2241049 | G | 0.386 | 0.3476 | A | 3.473 | 0.06238 | 1.18 | 15962234 | IL17R | |
| 4 | rs4694637 | G | 0.4016 | 0.4408 | A | 3.392 | 0.0655 | 0.8514 | 74977869 | IL8 | |
| 6 | rs9267853 | A | 0.2448 | 0.2799 | G | 3.377 | 0.06613 | 0.8342 | 32303229 | Chr6 Mapping | |
| 22 | rs9606603 | A | 0.4896 | 0.4508 | T | 3.287 | 0.06983 | 1.169 | 15936067 | IL17R | |

FIG. 15B

| | | | | | | | |
|---|---|---|---|---|---|---|---|
| 4 | rs4694178 | C | 0.4016 | 0.4392 | A | 3.137 | 0.07652 | 0.8567 | 74977723 | IL8 |
| 19 | rs2277984 | A | 0.4663 | 0.5039 | G | 3.052 | 0.08062 | 0.8604 | 6630511 | TNFSF14 (LIGHT) |
| 14 | rs12891812 | C | 0.101 | 0.1249 | A | 2.957 | 0.08548 | 0.7877 | 23417976 | Chr14 Mapping |
| 4 | rs1609798 | A | 0.274 | 0.3078 | G | 2.939 | 0.08648 | 0.8489 | 103894643 | NFKB1 |
| 1 | rs11804284 | A | 0.09326 | 0.116 | G | 2.881 | 0.08963 | 0.7837 | 67411275 | IL23R |
| 6 | rs10484879 | A | 0.2526 | 0.2221 | C | 2.831 | 0.09249 | 1.184 | 52159916 | IL17 |
| 6 | rs3134798 | G | 0.1802 | 0.2091 | A | 2.812 | 0.09358 | 0.8311 | 32292683 | Chr6 Mapping |
| 19 | rs379527 | C | 0.387 | 0.3523 | A | 2.811 | 0.09359 | 1.161 | 6627442 | TNFSF14 (LIGHT) |

FIG. 16A

| CHR | SNP | A1 | F_A | F_U | A2 | CHISQ | P | OR | Location | Gene Name | Comments |
|---|---|---|---|---|---|---|---|---|---|---|---|
| 1 | rs1569922 | A | 0.2897 | 0.3636 | G | 11.75 | 0.0006078 | 0.7138 | 67376984 | IL23R | Interleukin 23 receptor |
| 14 | rs2231810 | A | 0.1659 | 0.1158 | G | 9.873 | 0.001677 | 1.518 | 22896659 | EFS | Embryonal Fyn-associated substrate isoform 1 |
| 14 | rs2231805 | A | 0.1606 | 0.1118 | G | 8.997 | 0.002704 | 1.52 | 22899004 | EFS | Embryonal Fyn-associated substrate isoform 1 |
| 14 | rs1951731 | G | 0.1808 | 0.1314 | A | 8.866 | 0.002905 | 1.459 | 23433381 | Chr14 Mapping | C14orf165 |
| 14 | rs1958300 | T | 0.3806 | 0.3241 | A | 6.656 | 0.009883 | 1.281 | 23400032 | Chr14 Mapping | Unknown gene |
| 14 | rs7148564 | A | 0.1964 | 0.1532 | T | 6.205 | 0.01274 | 1.352 | 22893753 | Chr14 Mapping | Unknown gene |
| 19 | rs1799969 | A | 0.05915 | 0.08911 | G | 6.14 | 0.01322 | 0.6427 | 10255792 | ICAM1 | Intercellular adhesion molecule 1 |
| 4 | rs1609798 | A | 0.2652 | 0.3165 | G | 6.012 | 0.01421 | 0.7794 | 103894643 | NFKB1 | Nuclear factor kappa-B, subunit 1 |
| 1 | rs11209008 | A | 0.01674 | 0.03261 | G | 4.879 | 0.02718 | 0.5051 | 67335319 | IL23R | Interleukin 23 receptor |
| 14 | rs10130976 | A | 0.03906 | 0.02183 | T | 4.853 | 0.0276 | 1.822 | 224774546 | Chr14 Mapping | Unknown gene |
| 14 | rs10149449 | G | 0.115 | 0.08498 | A | 4.785 | 0.02871 | 1.399 | 22910351 | Chr14 Mapping | Interleukin 25 |
| 10 | rs1399180 | A | 0.1293 | 0.164 | G | 4.51 | 0.0337 | 0.7566 | 8138725 | GATA3 | GATA binding protein 3 isoform 1 |
| 19 | rs2234182 | A | 0.3534 | 0.4004 | G | 4.402 | 0.0359 | 0.8185 | 6486080 | TNFSF9 | tumor necrosis factor ligand 9 |
| 4 | rs3774965 | C | 0.02135 | 0.0377 | A | 4.338 | 0.03728 | 0.5568 | 103882128 | NFKB1 | Nuclear factor kappa-B, subunit 1 |
| 10 | rs1244186 | A | 0.2221 | 0.2628 | G | 4.281 | 0.03854 | 0.8007 | 8132689 | GATA3 | GATA binding protein 3 isoform 1 |
| 6 | rs10484879 | A | 0.2556 | 0.2154 | C | 4.274 | 0.0387 | 1.25 | 52159916 | IL17 | Interleukin 17 |
| 19 | rs375947 | G | 0.3135 | 0.3581 | A | 4.217 | 0.04003 | 0.8184 | 180441451 | IL12RB1 | Interleukin 12 receptor beta subunit isoform 1 |
| 1 | rs2229579 | A | 0.1272 | 0.09802 | G | 4.082 | 0.04335 | 1.341 | 23946468 | CNR2 | Cannabinoid receptor 2 (macrophage) |
| 6 | rs9296012 | A | 0.2109 | 0.1749 | G | 3.981 | 0.04602 | 1.261 | 32303310 | Chr6 Mapping | Notch 4 |
| 1 | rs1004819 | A | 0.4141 | 0.3696 | G | 3.954 | 0.04677 | 1.205 | 67382234 | IL23R | Interleukin 23 receptor |
| 4 | rs3774968 | A | 0.4764 | 0.4315 | G | 3.839 | 0.05008 | 1.199 | 103888305 | NFKB1 | |
| 14 | rs11160711 | A | 0.4107 | 0.3681 | G | 3.635 | 0.05658 | 1.197 | 19983836 | Chr14 Mapping | |
| 14 | rs755777 | G | 0.173 | 0.1413 | A | 3.621 | 0.05707 | 1.271 | 20016772 | Chr14 Mapping | |
| 12 | rs1001449 | A | 0.01451 | 0.02668 | G | 3.43 | 0.06403 | 0.5371 | 10156362 | CLEC7A (Dectin) TNFSF14 (LIGHT) | |
| 19 | rs2277984 | A | 0.4665 | 0.5089 | G | 3.415 | 0.0646 | 0.8439 | 6630511 | | |
| 6 | rs77447909 | A | 0.2556 | 0.2198 | G | 3.365 | 0.06661 | 1.219 | 52162208 | IL17 | |
| 10 | rs528778 | A | 0.1652 | 0.1976 | G | 3.356 | 0.06697 | 0.8033 | 8152149 | GATA3 | |

FIG. 16B

| Chr | rs# | A1 | f1 | f2 | A2 | stat | p | OR | position | gene | notes |
|---|---|---|---|---|---|---|---|---|---|---|---|
| 19 | rs379527 | C | 0.3789 | 0.3389 | A | 3.3 | 0.06926 | 1.19 | 6627442 | TNFSF14 (LIGHT) | |
| 1 | rs1343151 | A | 0.2567 | 0.2935 | G | 3.216 | 0.07292 | 0.8314 | 67431150 | IL23R | |
| 1 | rs16828926 | A | 0.1741 | 0.1443 | G | 3.176 | 0.07473 | 1.25 | 23960436 | CNR2 | |
| 1 | rs2501390 | A | 0.1763 | 0.1465 | G | 3.13 | 0.07689 | 1.247 | 23961102 | CNR2 | |
| 1 | rs2502965 | G | 0.1763 | 0.1472 | A | 2.982 | 0.0842 | 1.24 | 23963582 | CNR2 | |
| 14 | rs12891812 | C | 0.1016 | 0.1265 | A | 2.905 | 0.08833 | 0.7807 | 23417976 | Chr14 Mapping | |
| 23 | rs3764879 | G | 0.3379 | 0.2969 | C | 2.724 | 0.09886 | 1.208 | 12684354 | TLR8 | |
| 3 | rs2633582 | C | 0.1004 | 0.07905 | A | 2.68 | 0.1016 | 1.301 | 113702030 | BTLA | |
| 6 | rs4711998 | A | 0.221 | 0.253 | G | 2.681 | 0.1016 | 0.8377 | 52158312 | IL17 | |
| 4 | rs3774932 | A | 0.4978 | 0.4603 | G | 2.655 | 0.1032 | 1.162 | 103781378 | NFKB1 | |
| 1 | rs3138156 | G | 0.05682 | 0.07555 | A | 2.641 | 0.1041 | 0.7372 | 6457696 | TNFRSF25 (DR3) | |
| 12 | rs12580050 | T | 0.3599 | 0.3958 | C | 2.601 | 0.1068 | 0.8581 | 51586470 | KRT8/KRT18 | Questionable but WORK |
| 14 | rs10143597 | A | 0.3337 | 0.2994 | G | 2.589 | 0.1076 | 1.172 | 22912579 | Chr14 Mapping | |
| 3 | rs9288953 | A | 0.2958 | 0.3297 | G | 2.541 | 0.1109 | 0.8538 | 113685942 | BTLA | |
| 12 | rs1544410 | A | 0.3915 | 0.4269 | C | 2.456 | 0.1171 | 0.8638 | 46526102 | VDR | |
| 22 | rs721930 | G | 0.2242 | 0.195 | A | 2.44 | 0.1183 | 1.193 | 15960362 | IL17R | |
| 14 | rs10137082 | A | 0.2652 | 0.2341 | G | 2.438 | 0.1185 | 1.18 | 22909873 | Chr14 Mapping | Questionable but WORK |
| 3 | rs2705534 | C | 0.1004 | 0.08004 | A | 2.426 | 0.1194 | 1.283 | 113691075 | BTLA | |
| 1 | rs11800462 | G | 0.05492 | 0.07256 | A | 2.418 | 0.12 | 0.7427 | 6458767 | TNFRSF25 (DR3) | |

METHODS OF IDENTIFYING THE GENETIC BASIS OF A DISEASE BY A COMBINATORIAL GENOMICS APPROACH, BIOLOGICAL PATHWAY APPROACH, AND SEQUENTIAL APPROACH

The present application claims the benefit of priority under 35 U.S.C. §119(e) of provisional application Ser. No. 60/938,796, filed May 18, 2007, and of provisional application Ser. No. 60/939,568, filed May 22, 2007, both of which contents are hereby incorporated by reference.

FIELD OF THE INVENTION

The invention relates generally to the fields of medicine and genetics.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Advances in genetics and medicine has led to the understanding that most diseases have a genetic component. For example, variants in the sequence of DNA in an individual may impact a disease by producing variants in the proteins encoded. These encoded proteins; in turn, may perform biological functions that will become altered by the genetic variants. Furthermore, it has become understood that complex diseases often result from the interactions of several genes or their products, each with varying patterns of mutations. By understanding the underlying genetics of a disease or condition, one may find therapeutic targets or opportunities for diagnostics, variants that act as potential susceptibility or protective markers of a disease, or pathways for further research. Thus, there is an enormous need in the art to identify genes, genetic variants and biological pathways that are associated with a disease or condition.

SUMMARY OF THE INVENTION

Various embodiments provide methods of identifying a gene and/or genetic variant involved in the pathogenesis of a disease, the method comprising the steps of performing a genetic association study of a plurality of subjects clinically diagnosed with the disease, using an immune response to an antigen to stratify the disease into one or more subdivisions, and identifying the gene and/or genetic variant involved in the pathogenesis of the disease by clustering statistically significant genetic markers around one or more subdivisions of the disease. In another embodiment, the disease is inflammatory bowel disease. In another embodiment, the genetic association study comprises a whole genome association study. In another embodiment, the genetic association study comprises the use of a haplotype-defined gene structure. In another embodiment, the genetic association study comprises the use of high throughput screening. In another embodiment, the immune response comprises Ab-ASCA, Ab-Cbir1, Ab-I2, Ab-OmpC and/or Ab-pANCA.

Other embodiments provide methods of identifying a biological pathway involved in the pathogenesis of a disease, comprising utilizing an immune expression profile as a quantitative trait to scan the genome of an individual to identify one or more candidate genes, and identifying the biological pathway based upon the presence of one or more candidate genes. In another embodiment, the disease is inflammatory bowel disease. In another embodiment, the immune expression profile comprise the use of Ab-ASCA, Ab-Cbir1, Ab-I2, Ab-OmpC and/or Ab-pANCA.

Other embodiments provide methods of treating a disease, comprising using a combinatorial genomics approach to identify genes, genetic variants and/or biological pathways associated with the disease, and treating the disease. In another embodiment, the disease is inflammatory bowel disease.

Various other embodiments provide methods of treating a disease, comprising using a biological pathway approach to identify genes, genetic variants and/or biological pathways associated with the disease, and treating the disease. In another embodiment, the disease is inflammatory bowel disease.

Other embodiments provide methods of treating a disease, comprising using a sequential approach to identify genes, genetic variants and/or biological pathways associated with the disease, and treating the disease. In another embodiment, the disease is inflammatory bowel disease.

Other embodiments provide methods for discovering the mechanism of a disease, comprising clustering statistically significant genetic markers around a subclinical phenotypic trait, identifying an associated biological pathway, and discovering the mechanism of the disease based upon the associated biological pathway identified.

Other features and advantages of the invention will become apparent from the following detailed description, taken in conjunction with the accompanying drawings, which illustrate, by way of example, various embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIG. 4 (prior art) depicts an example of antigens known to be associated with a disease.

FIG. 5 (prior art) depicts an example of results of independent associations of antibodies, genetic variants, and disease phenotypes (multiple logistic regression). The two associations in the UC-like column are negative associations, while the other columns are positive associations.

FIG. 6 (prior art) depicts a chart as an example of how after whole genome analysis identifies gene variants in a given individual, bioinformatics link gene variants into pathways. The figure depicts integrated pathways discovery clustering of genetic variants by antibody response.

FIGS. 10A-10T depict examples of results generated by the Sequential Approach (Combinatorial Genomics Approach followed by Biological Pathway Approach). The figures list a chart of statistically significant associations, organized by columns describing chromosome, position, dbsnp 126, SNP, importance, p-value by permutation test, antibodies, measurement, transformation, gene ID, gene, and gene description.

FIGS. 11A-11B depict examples of results generated by the Sequential Approach. The figures list statistically significant associations of IGA ASCA with corresponding genetic variants.

FIGS. 12A-12B depict examples of results generated by the Sequential Approach. The figures list statistically significant associations of IGG ASCA with corresponding genetic variants.

FIGS. 13A-13B depict examples of results generated by the Sequential Approach. The figures list statistically significant associations of OMPC with corresponding genetic variants.

FIG. 14 depicts examples of results generated by the Sequential Approach. This figure lists statistically significant associations of I2 with corresponding genetic variants.

FIGS. 15A-15B depict examples of results generated by the Sequential Approach. The figures list statistically significant associations of ASCA with corresponding genetic variants.

FIGS. 16A-16B depict examples of results generated by the Sequential Approach. The figures list statistically significant associations of anti-Cbir1 flagellin with corresponding genetic variants.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

"Haplotype" as used herein refers to a set of single nucleotide polymorphisms (SNPs) on a gene or chromatid that are statistically associated.

"Protective" and "protection" as used herein refer to a decrease in susceptibility to a disease, including but not limited to CD and UC.

"Odds ratio" as used herein refers to the probability of having a disease if one has the gene, as compared to one who does not have the gene.

"Population attributable risk" as used herein refers to the proportion of the total disease risk due to the particular gene.

As used herein, the term "biological sample" means any biological material from which nucleic acid molecules can be prepared. As non-limiting examples, the term material encompasses whole blood, plasma, saliva, cheek swab, or other bodily fluid or tissue that contains nucleic acid.

Combinatorial Genomics Approach

Figure 1:
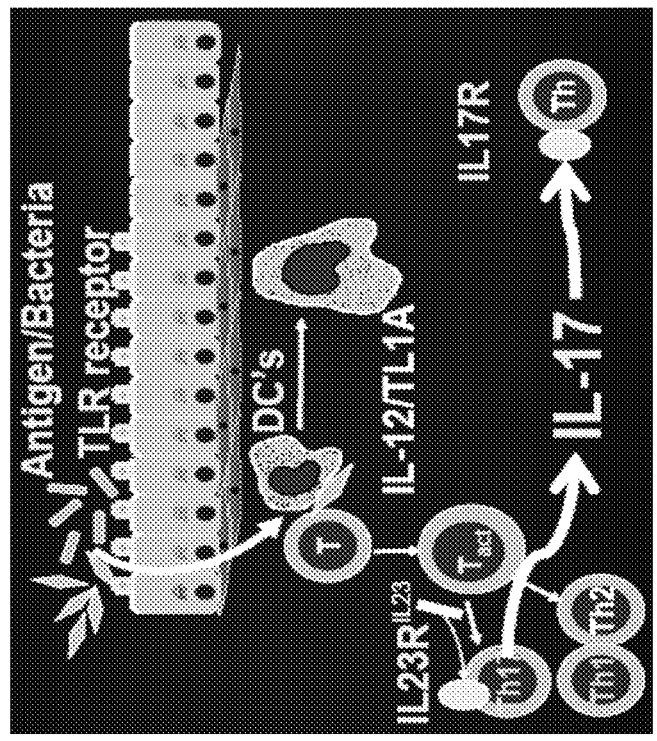
FIG. 1 (prior art) depicts an example of how knowledge of potential biologic interactions can be combined with haplotype-defined gene structure. (a) a diagram of the pathogenesis of Crohn's. Disease; (b) a chart of an example of haplotype defined gene interactions.
Figure 2:
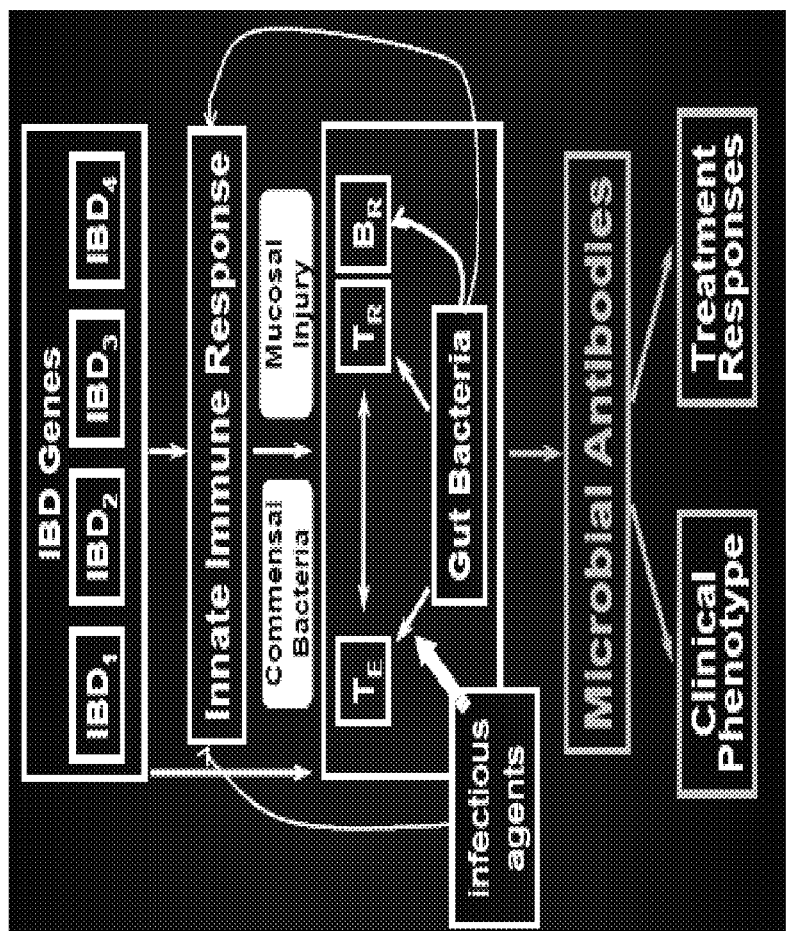
FIG. 2 (prior art) depicts a diagram demonstrating how genes can alter the immune response to different environmental organisms.
Figure 3:
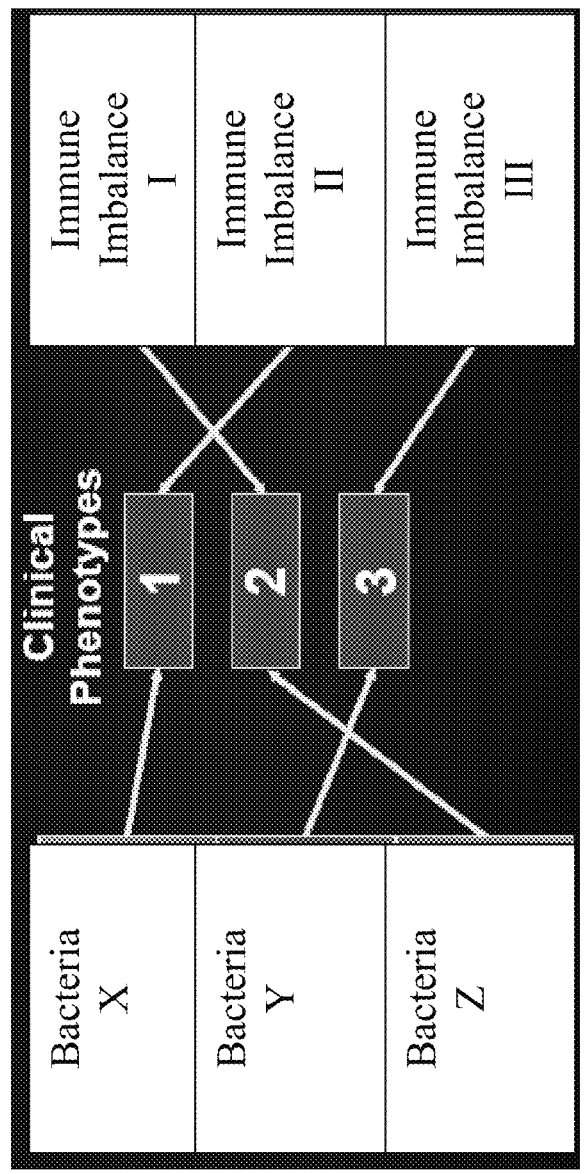
FIG. 3 (prior art) depicts a diagram demonstrating an example of how a clinical phenotype may be the result of bacteria and immune balance in the pathogenesis of a disease.
Figure 7:
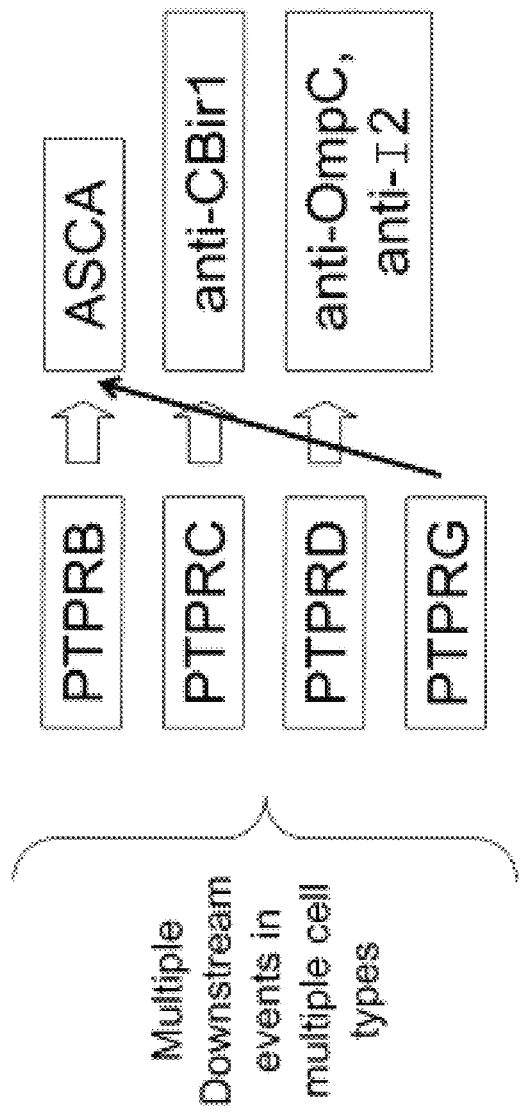
FIG. 7 (prior art) depicts an example related to the protein tyrosine phosphatase receptor family. Each is in a different specific cell type and pathogenetically-associated process.
Figure 8:
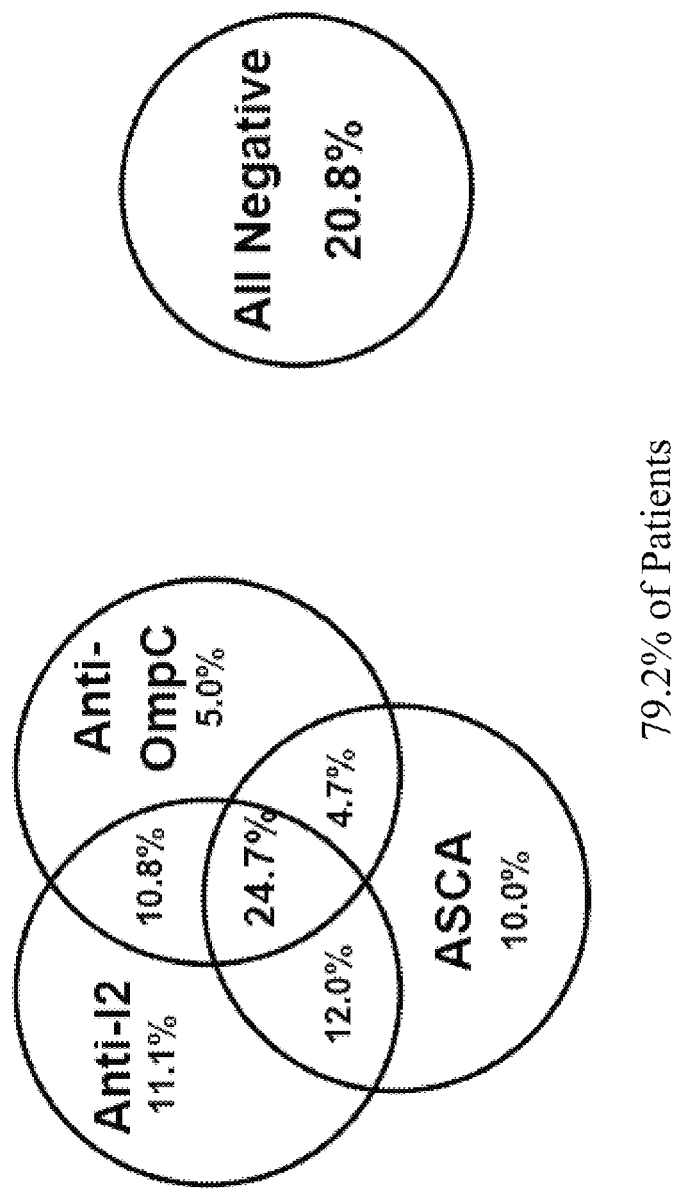
FIG. 8 (prior art) depicts a diagram depicting an example of combinations of antibodies. The figure describes qualitative responses to multiple microbial antigens.
Figure 9:
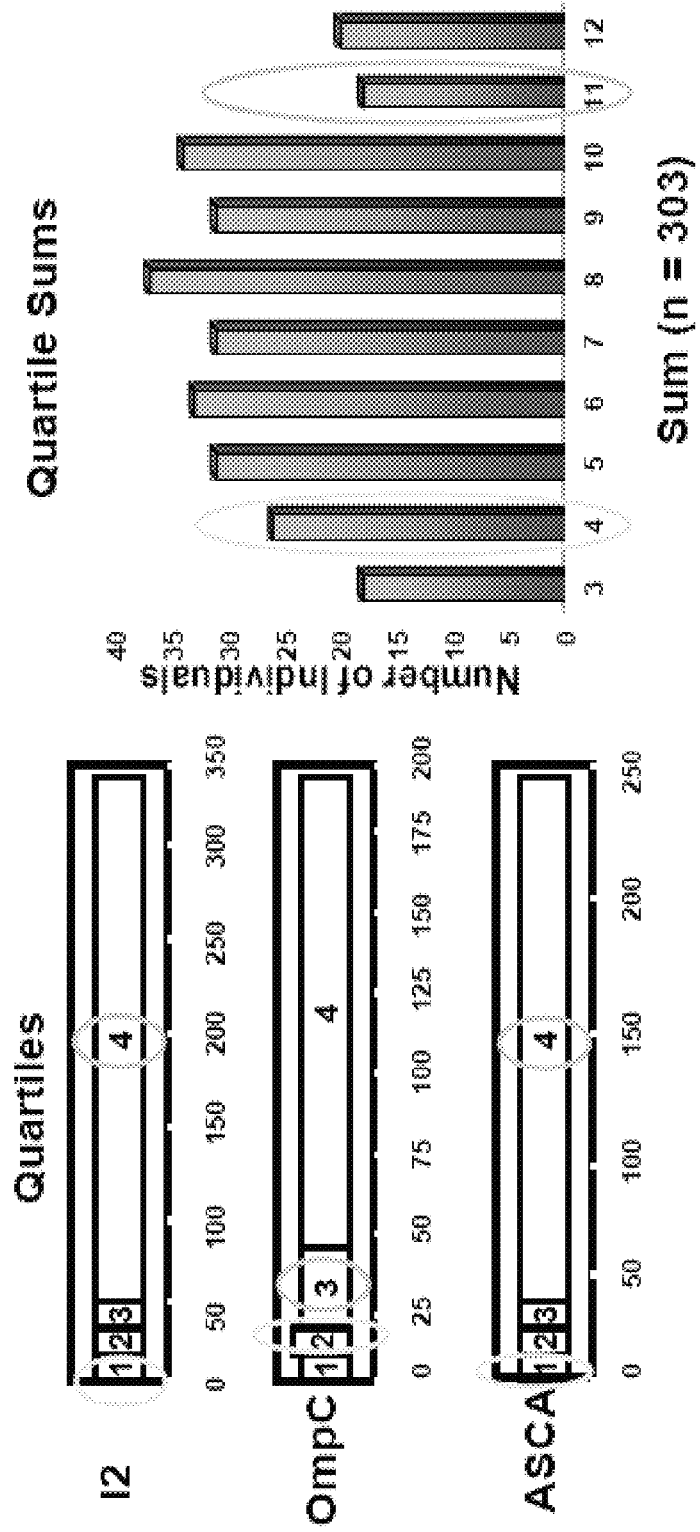
FIG. 9 (prior art) depicts a graph as an example, demonstrating how quantitative response can be represented by quartiles for each microbial antigen.
Figure 17:
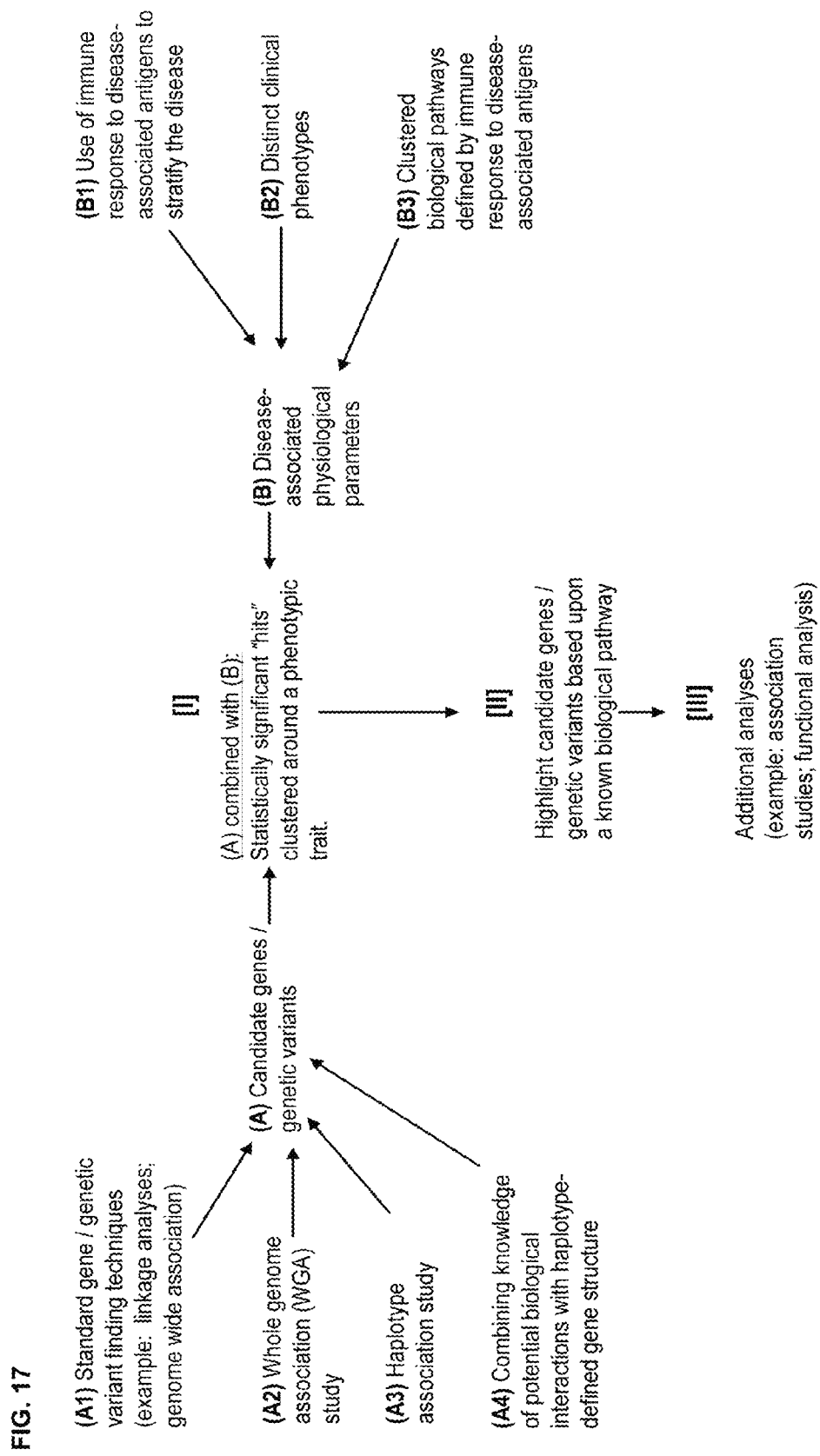
FIG. 17 depicts a flow chart of an example of the Sequential Approach, where the Combinatorial Genomics Approach (I) is followed sequentially by the Biological Pathway Approach (II, III).

As disclosed herein, the inventors utilized disease-associated physiological parameters (FIG. 17, (B)), both individual and combined, as quantitative traits to scan the entire genome in an attempt to focus in on regions where informative genes might be discovered. Alternatively, the quantitative traits may also be used in conjunction with one or more candidate genes/genetic variants (FIG. 17, (A)). The quantitative traits are utilized to create a specific subcategory of a disease, as opposed to current techniques, which rely on targets that emerge from studies of the disease as a whole. This approach has yielded statistically significant hits across the whole genome in genes and areas that would not have previously been thought relevant, yet clearly are relevant after additional bioinformatics and biologic analyses. The statistically significant hits are thus clustered around a subclinical phenotypic trait and suggest a pathway that can be further explored.

In one embodiment, the present invention provides methods of identifying genes and genetic variants that, either alone or in combination, are important to the pathogenesis of a disease comprising the following steps: whole genome association study of subjects clinically diagnosed with a disease (FIG. 17, A2); haplotype association study of subjects clinically diagnosed with inflammatory bowel disease (FIG. 17, A3); combine data of potential biological interactions with haplotype-defined gene structure (FIG. 17, A4); use of immune response to disease-associated antigens to stratify the disease (FIG. 17, B1); clustering biological pathways in individuals defined by immune response to disease-associated antigens (FIG. 17, B3).

In another embodiment, the disease-associated physiological parameters (FIG. 17, (B)) are distinct clinical phenotypes (FIG. 17, B2). In another embodiment, the whole genome association study (FIG. 17, A2) uses known genetic markers. In another embodiment, the whole genome association study (FIG. 17, A2) uses SNPs. In another embodiment, the whole genome association study (FIG. 17, A2) describes biological and/or statistical interactions between genes. In another embodiment, the haplotype association study (FIG. 17, A3) captures the true extent of the Population Attributable Risk. In another embodiment, the haplotype association study (FIG. 17, A3) provides rapid identification of high-impact subjects to be sequenced.

In another embodiment, the identification of genes and genetic variants that, either alone or in combination, are important to the pathogenesis of a disease, provide methods of identifying biological pathways that, either alone or in combination, are important to the pathogenesis of the disease.

In another embodiment, the identification of genes and genetic variants that either alone or in combination, are important to the pathogenesis of a disease, provide methods of identifying biological pathways that, either alone or in combination, are important to the pathogenesis of an alternative disease. In another embodiment, the identification of genes and genetic variants that, either alone or in combination, are important to the pathogenesis of a disease, provide methods of identifying additional genes and genetic variants that, either alone or in combination, are important to the pathogenesis of the disease. In another embodiment, the identification of genes and genetic variants that, either alone or in combination, are important to the pathogenesis of a disease, provide methods of identifying additional genes and genetic variants that, either alone or in combination, are important to the pathogenesis of an alternative disease. In another embodiment, the identification of the genes and/or genetic variants allow functional analysis specific to an individual being treated. In another embodiment, the functional analysis allows a targeted and effective treatment for the individual, where the individual is treated by inhibiting or enhancing the products of the genes and/or genetic variants.

In another embodiment, the present invention provides methods of treatment of a disease in an individual by the following steps: determine the presence of integrated pathogenic pathways in the individual; diagnose the individual for a disease subtype; administer therapy combinations specific to the individual's disease diagnosis. In another embodiment, the present invention provides methods of treatment of a disease in an individual by the following steps: determine the presence of integrated pathogenic pathways in the individual; diagnose the individual for a disease subtype; target integrated pathogenic pathways for inhibition.

In one embodiment, the present invention provides a kit that includes at least one of the following: genetic markers, haplotypes, and antibodies. In another embodiment, the kit includes antibodies to stratify the disease.

In one embodiment, the present invention provides methods of diagnosing susceptibility to a disease by determining the presence or absence of immune responses to antigen. In another embodiment, the present invention provides methods of diagnosing susceptibility to a specific subtype of a disease by determining the presence or absence of immune responses to antigen.

In another embodiment, the present invention provides methods of prognosis of a disease by determining the presence or absence of immune responses to antigen. In another embodiment, the present invention provides methods of treatment of a disease by inhibiting expression of immune responses to antigen.

In another embodiment, the present invention provides methods to vaccinate an individual in need thereof against a disease, by administering a composition that includes antigen to disease-associated antibodies. In another embodiment, the antigen to disease-associated antibodies modulate innate immunity in the individual.

In another embodiment, the present invention provides methods of diagnosing susceptibility to a disease in an individual by identifying genes and genetic variants that, either alone or in combination, are important to the pathogenesis of the disease. In another embodiment, the present invention provides methods of prognosis of a disease in an individual by identifying genes and genetic variants that, either alone or in combination, are important to the pathogenesis of the disease. In another embodiment, the present invention provides methods of treatment of a disease in an individual by inhibiting identified genes and genetic variants that, either alone or in combination, are important to the pathogenesis of the disease.

In one embodiment, the present invention provides methods of providing functional constructs of genes and genetic variants that, either alone or in combination, are important to the pathogenesis of a disease comprising the following steps: identify genes and genetic variants that, while not apparent as associated with a subclinical phenotypic trait as a whole, are associated with specific antibodies of the subclinical phenotypic trait. In another embodiment, the functional construct of genes and genetic variants provide identification of additional genes and genetic variants that, either alone or in combination, are important to the pathogenesis of the disease.

Biological Pathway Approach

As disclosed herein, the inventors highlighted candidate genes/genetic variants based upon a known biological pathway (FIG. 17, II), but whose role in a disease and/or disorder had not yet been identified prior, to scan DNA samples of a case-control cohort. Candidate genes are thus interrogated in combination. From the group of highlighted candidate genes/genetic variants (FIG. 17, II), additional analyses (FIG. 17, III) are utilized to narrow relevant genes further.

In one embodiment, the present invention provides methods of identifying genes and genetic variants that, either alone or in combination, are important to the pathogenesis of a disease comprising the following steps: highlighting candidate genes/genetic variants based upon a known biological pathway (FIG. 17, II); additional analyses to narrow the relevant genes further (FIG. 17, III). In another embodiment, the genetic variants are SNPs and/or haplotypes. In another embodiment, the additional analyses is functional analysis, association studies and/or standard genetic techniques.

In another embodiment, the identification of genes and genetic variants that, either alone or in combination, are important to the pathogenesis of a disease, provide methods of identifying targets for treatment and/or therapy. In another embodiment, the present invention provides methods of treatment of a disease by inhibiting the product of genes and genetic variants that have been identified as, either alone or in combination, important to the pathogenesis of the disease. In another embodiment, the present invention provides methods of treatment of a disease by enhancing the product of genes and genetic variants that have been identified as, either alone or in combination, important for protection against the pathogenesis of the disease.

In one embodiment, the present invention provides methods of identifying additional pathways that, either alone or in combination, are important to the pathogenesis of a disease comprising the following steps: selecting. SNPs for genes related to a pathway possibly involved with a disease; genotyping SNPs in a disease case-control cohort; establishing haplotypes from SNPs genotyped; test for association of SNPs with disease; utilizing associated SNPs, test for association of additional genes and genetic variants in a related pathway.

In one embodiment, the present invention provides a kit that includes at least one of: SNPs, haplotypes, and genotyping assays.

In another embodiment, the present invention provides methods of diagnosing susceptibility for a disease in an individual by identifying genes and genetic variants in the individual that, either alone or in combination, are important to the pathogenesis of the disease. In another embodiment, the present invention provides methods of prognosis of a disease in an individual by identifying genes and genetic variants that, either alone or in combination, are important to the pathogenesis of the disease. In another embodiment, the present invention provides methods of treatment of a disease in an individual by inhibiting the product of genes and genetic variants that, either alone or in combination, are important to the pathogenesis of the disease. In another embodiment, the present invention provides methods of treatment of disease in an individual by enhancing the product of genes and genetic variants that, either alone or in combination, are important for protection against the pathogenesis of the disease.

Sequential Approach

Combinatorial Genomics Approach followed by Biological Pathway Approach

As disclosed herein, the inventors utilized a Sequential Approach whereby the Biological Pathway Approach is used as an extension of the Combinatorial Genomics Approach. In the Sequential Approach, inventors utilize disease-associated physiological parameters (FIG. 17, B), both individual and combined, as quantitative traits to scan the entire genome in an attempt to focus in on regions where informative genes might be discovered. The statistically significant hits are thus clustered around a phenotypic trait (FIG. 17, I) and suggest a pathway that can be further explored with the Biological Pathway Approach. Candidate genes are then interrogated in combination, highlighted based upon a known biological pathway that is possibly involved in the disease and/or disorder (FIG. 17, II), and may undergo additional analyses (FIG. 17, III) to identify additional biological pathways, genes and/or genetic variants.

In one embodiment, the present invention provides methods of identifying genes and genetic variants that, either alone or in combination, are important to the pathogenesis of a disease comprising the following steps: cluster statistically significant hits around a phenotypic trait (FIG. 17, I), highlighting candidate genes/genetic variants based upon a known biological pathway (FIG. 17, II), followed sequentially by additional analyses (FIG. 17, III).

Variety of Methods and Materials

A variety of methods can be used to determine the presence or absence of a variant allele or haplotype. As an example, enzymatic amplification of nucleic acid from an individual may be used to obtain nucleic acid for subsequent analysis. The presence or absence of a variant allele or haplotype may also be determined directly from the individual's nucleic acid without enzymatic amplification.

Analysis of the nucleic acid from an individual, whether amplified or not, may be performed using any of various techniques. Useful techniques include, without limitation, polymerase chain reaction based analysis, sequence analysis and electrophoretic analysis. As used herein, the term "nucleic acid" means a polynucleotide such as a single or double-stranded DNA or RNA molecule including, for example, genomic DNA, cDNA and mRNA. The term nucleic acid encompasses nucleic acid molecules of both natural and synthetic origin as well as molecules of linear, circular or branched configuration representing either the sense or antisense strand, or both, of a native nucleic acid molecule.

The presence or absence of a variant allele or haplotype may involve amplification of an individual's nucleic acid by the polymerase chain reaction. Use of the polymerase chain reaction for the amplification of nucleic acids is well known in the art (see, for example, Mullis et al. (Eds.), The Polymerase Chain Reaction, Birkhauser, Boston, (1994)).

A TaqmanB allelic discrimination assay available from Applied Biosystems may be useful for determining the presence or absence of, simply by way of example, a TL1A variant allele. As will be readily appreciated by those of skill in the art, numerous other genes, variant alleles and/or haplotypes can be studied in this fashion. In a TaqmanB allelic discrimination assay, a specific, fluorescent, dye-labeled probe for each allele is constructed. The probes contain different fluorescent reporter dyes such as FAM and VICTM to differentiate the amplification of each allele. In addition, each probe has a quencher dye at one end which quenches fluorescence by fluorescence resonant energy transfer (FRET). During PCR, each probe anneals specifically to complementary sequences in the nucleic acid from the individual. The 5' nuclease activity of Taq polymerase is used to cleave only probe that hybridize to the allele. Cleavage separates the reporter dye from the quencher dye, resulting in increased fluorescence by the reporter dye. Thus, the fluorescence signal generated by PCR amplification indicates which alleles are present in the sample. Mismatches between a probe and allele reduce the efficiency of both probe hybridization and cleavage by Taq polymerase, resulting in little to no fluorescent signal. Improved specificity in allelic discrimination assays can be achieved by conjugating a DNA minor grove binder (MGB) group to a DNA probe as described, for example, in Kutyavin et al., "3'-minor groove binder-DNA probes increase sequence specificity at PCR extension temperature, "Nucleic Acids Research 28:655-661 (2000)). Minor grove binders include, but are not limited to, compounds such as dihydrocyclopyrroloindole tripeptide (DPI).

Sequence analysis also may also be useful for determining the presence or absence of a variant allele or haplotype. As will be readily appreciated by those of skill in the art, numerous other genes, variant alleles and/or haplotypes can be studied in this fashion.

Restriction fragment length polymorphism (RFLP) analysis may also be useful for determining the presence or absence of a particular allele (Jarcho et al. in Dracopoli et al., Current Protocols in Human Genetics pages 2.7.1-2.7.5, John Wiley & Sons, New York; Innis et al., (Ed.), PCR Protocols, San Diego: Academic Press, Inc. (1990)). As used herein, restriction fragment length polymorphism analysis is any method for distinguishing genetic polymorphisms using a restriction enzyme, which is an endonuclease that catalyzes the degradation of nucleic acid and recognizes a specific base sequence, generally a palindrome or inverted repeat. One skilled in the art understands that the use of RFLP analysis depends upon an enzyme that can differentiate two alleles at a polymorphic site.

Allele-specific oligonucleotide hybridization may also be used to detect a disease-predisposing allele. Allele-specific oligonucleotide hybridization is based on the use of a labeled oligonucleotide probe having a sequence perfectly complementary, for example, to the sequence encompassing a disease-predisposing allele. Under appropriate conditions, the allele-specific probe hybridizes to a nucleic acid containing the disease-predisposing allele but does not hybridize to the one or more other alleles, which have one or more nucleotide mismatches as compared to the probe. If desired, a second allele-specific oligonucleotide probe that matches an alternate allele also can be used. Similarly, the technique of allele-specific oligonucleotide amplification can be used to selectively amplify, for example, a disease-predisposing allele by using an allele-specific oligonucleotide primer that is perfectly complementary to the nucleotide sequence of the disease-predisposing allele but which has one or more mismatches as compared to other alleles (Mullis et al., supra, (1994)). One skilled in the art understands that the one or more nucleotide mismatches that distinguish between the disease-predisposing allele and one or more other alleles are preferably located in the center of an allele-specific oligonucleotide primer to be used in allele-specific oligonucleotide hybridization. In contrast, an allele-specific oligonucleotide primer to be used in PCR amplification preferably contains the one or more nucleotide mismatches that distinguish between the disease-associated and other alleles at the 3' end of the primer.

A heteroduplex mobility assay (HMA) is another well known assay that may be used to detect a SNP or a haplotype. HMA is useful for detecting the presence of a polymorphic sequence since a DNA duplex carrying a mismatch has reduced mobility in a polyacrylamide gel compared to the mobility of a perfectly base-paired duplex (Detwart et al., Science 262:1257-1261 (1993); White et al., Genomics 12:301-306 (1992)).

The technique of single strand conformational, polymorphism (SSCP) also may be used to detect the presence or absence of a SNP and/or a haplotype (see Hayashi, K., Methods Applic. 1:34-38 (1991)). This technique can be used to detect mutations based on differences in the secondary structure of single-strand DNA that produce an altered electrophoretic mobility upon non-denaturing gel electrophoresis. Polymorphic fragments are detected by comparison of the electrophoretic pattern of the test fragment to corresponding standard fragments containing known alleles.

Denaturing gradient gel electrophoresis (DGGE) also may be used to detect a SNP and/or a haplotype. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (Sheffield et al., "Identifying DNA Polymorphisms by Denaturing Gradient Gel Electrophoresis" in Innis et al., supra, 1990).

Other molecular methods useful for determining the presence or absence of a SNP and/or a haplotype are known in the art and useful in the methods of the invention. Other well-known approaches for determining the presence or absence of a SNP and/or a haplotype include automated sequencing and RNAase mismatch techniques (Winter et al., Proc. Natl. Acad. Sci. 82:7575-7579 (1985)). Furthermore, one skilled in the art understands that, where the presence or absence of multiple alleles or haplotype(s) is to be determined, individual alleles can be detected by any combination of molecular methods. See, in general, Birren et al. (Eds.) Genome Analysis: A Laboratory Manual Volume 1 (Analyzing DNA) New York, Cold Spring Harbor Laboratory Press (1997). In addition, one skilled in the art understands that multiple alleles can be detected in individual reactions or in a single reaction (a "multiplex" assay). In view of the above, one skilled in the art realizes that the methods of the present invention for diagnosing or predicting susceptibility to or protection against CD, UC or other diseases in an individual may be practiced using one or any combination of the well known assays described above or another art-recognized genetic assay.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Combinatorial Genomics Approach Generally

The inventors utilized antibody expression profiles, both individual and combined, as quantitative traits to scan the entire genome to focus in on regions where informative genes might be discovered. The quantitative traits are utilized to create a specific subcategory of a disease, as opposed to current techniques, which rely on targets that emerge from studies of the disease as a whole. This approach has yielded statistically significant hits across the whole genome in genes and areas that would not have previously been thought relevant, yet clearly are relevant after additional bioinformatics and biologic analyses. The statistically significant hits are thus clustered around a subclinical phenotypic trait and suggest a pathway that can be further explored. A particularly inventive feature of the present invention, therefore, involves conducting a whole genome association study of individuals in whom antibodies have already been assessed in the aforementioned manner, so as to suggest particular pathways for exploration.

Example 2

Steps for a Combinatorial Genomics Approach (1) Conduct whole genome association study of subjects clinically diagnosed with inflammatory bowel disease; (2) Perform haplotype association study of subjects clinically diagnosed with inflammatory bowel disease; (3) Combine knowledge of potential biological interactions with haplotype-defined gene structure; (4) Use of antibodies to antigens to stratify the disease; (5) Use immune responses to discover unique genes; (5) Cluster pathways in individuals defined by immune response to antigens.

Example 3

Biological Pathway Approach

The inventors identified genes and genetic variants that, either alone or in combination, are important to the pathogenesis of inflammatory bowel disease comprising the following steps: (1) selecting TagSNPs for major Caucasian haplotypes in eight genes related to the IL12/IL23 pathway; (2) genotyped in a Crohn's Disease case-control cohort; (3) used to infer haplotypes; (4) and then tested for association with Crohn's Disease.

Example 4

Case-Control Cohort

The inventors recruited subjects at the Cedars-Sinai Medical Center Inflammatory Bowel Disease center under the approval of the Cedars-Sinai Medical Center Institutional Review Board. Disease phenotype was assigned using a combination of standard endoscopic, histological, and radiographic features. Ashkenazi Jewish ethnicity was assigned when one or more grandparents were of Ashkenazi Jewish origin.

Example 5

Selection of SNPs

SNPs were selected by applying the "Tagger" option in the program Haploview to data from the International HapMap Project. SNPs that "tagged" major Caucasian haplotypes and at the same time that were predicted to be compatible with the Illumina genotyping technology using the Illumina Assay Design Tool were genotyped in the initial phases of the study. Since the inventors were interested in major genetic effects for the study rather than rare alleles, the goal of "tagging" was to find a set of tagSNPs in linkage disequilibrium with all SNPs in the HapMap data with a minor allele frequency≤5%; in some cases this goal was not completely met due to the limitations of the Illumina technology. A few SNPs were also added that were: 1) non-synonymous and had a minor allele frequency greater than 3%, 2) redundant in order to accommodate some assay failure in the initial Illumine run, and 3) markers suggested by information provided by SeattleSNPs. SNPs showing positive associations were selected for further genotyping by ABI technology.

Example 6

Genotyping

DNA was isolated from Epstein Barr virus transformed lymphoblastoid cell lines using proteinase K digestion, organic extraction, and ethanol precipitation. Single nucleotide markers (SNPs) were genotyped using one of two methods: (1) the oligonucleotide ligation assay, Illumine Golden Gate technology, following the manufacturer's protocol (Illumina, San Diego, Calif.), and (2) the 5'-extension reaction, TaqMan MGB technology, following the manufacturer's protocol (Applied Biosystems). Consistency of SNP genotyping between the two methods was checked for each SNP by genotyping 100 samples with both methods.

Example 7

Statistical Analyses

Haplotype blocks were determined using the "Tagger" routine of the program Haploview. Haplotypes of subjects were inferred from the genotyping data using the program PHASE v2. The association of the presence of a haplotype was tested using the chi-square test and the significance of results was assessed by applying a permutation test to the data in order to correct for multiple testing due to the number of haplotypes. Results with significance were defined by p<0.05 by permutation test. Due to sample size considerations, the results were for all CD and control subjects with Jewish and non-Jewish subjects combined. The notable exception to this was that an IL17A "risk" haplotype specific to the non-Jewish population was identified in the hypothesis-generating phase of the study and used for subsequent gene-gene interaction studies. Population attributable risk was estimated by assuming that 1) the frequency of a particular haplotype in the controls reflected the population frequency of that haplotype, and 2) the odds ratio for the association of a given haplotype reflected the relative risk of that haplotype for Crohn's disease. Haplotypes were numbered in order of frequency in controls (H1, H2, and so forth) and the nucleotides for each tagSNP listed according to the forward strand of the NCBI human genome build 36 and dbSNP. A "major" haplotype is a haplotype with a population frequency greater than 5% in the controls.

Example 8

TABLE 1

Statistically significant associations, as organized by clusters of Cbir1 antibodies and pathway-related clustering of genes.

| PATHWAY: | CORRESPONDING GENE: |
|---|---|
| TCR Activation | TCR alpha |
|  | PRPTC |
|  | NGAT5 |
| Transcription | 1KBKAP |
|  | F1B1 |
|  | RA17 |
| Endothelial Response | ZF124-VEGF |
| Myeloid Activation | TLR8 |

Example 9

TABLE 2

Statistically significant associations, as organized by clusters of 12 antibodies and pathway-related clustering of genes.

| PATHWAY: | CORRESPONDING GENE: |
|---|---|
| Innate Cell Signaling/Channels/GTPase. | KCNMAI (CGD - phenocopy) |
|  | K1D676 |
|  | S1PAL2 |
|  | SRGAP3 |
|  | RHOU |
| TCR Activation | TCR alpha |
|  | PAK7 |

Example 10

TABLE 3

Statistically significant associations, as organized by clusters of ASCA antibodies and pathway-related clustering of genes.

| PATHWAY: | CORRESPONDING GENE: |
|---|---|
| Cell Activation/Endosome | EHD3 |
|  | SRGAP3 |
|  | CDC42 (RAL) |
| Adherence | PTPRB |
| TCR Activation | BTNL2 |
|  | SAR (MHC-II) |
|  | PAK7 |
| Innate Channel | KCNMA1 |

Example 11

TABLE 4

Statistically significant associations, as organized by clusters of OmpC antibodies and pathway-related clustering of genes.

| PATHWAY: | CORRESPONDING GENE: |
|---|---|
| Myeloidal Function | PTPRD |
| NRXN3 Adhesion | NRXN3 |

Example 12

TABLE 5

Statistically significant associations, as organized by all antibodies (Cbir1, I2, ASCA, OmpC) and pathway-related clustering of genes.

| PATHWAY: | CORRESPONDING GENE: |
|---|---|
| TCR-alpha T cell | |
| Innate Activation | KCNMA1 |
| Extracellular Matrix | CHSS 11 |
| Transactivation - ZNF780 | NBPLD3 |
| Neral - NRXN3 | |

While the description above refers to particular embodiments of the present invention, it should be readily apparent to people of ordinary skill in the art that a number of modifications may be made without departing from the spirit thereof. The presently disclosed embodiments are, therefore, to be considered in all respects as illustrative and not restrictive. One skilled in the art will recognize many methods and materials similar or equivalent to those described herein, which could be used in the practice of the present invention. Indeed, the present invention is in no way limited to the methods and materials described. Furthermore, one of skill in the art would recognize that the invention can be applied to any number of conditions and disorders and diseases. It will also be readily apparent to one of skill in the art that the invention can be used in conjunction with a variety of phenotypes, such as serological markers, additional genetic variants, biochemical markers, abnormally expressed biological pathways, and variable clinical manifestations.

The invention claimed is:

1. A method for determining whether a gene variant and/or a genetic variant has involvement in the pathogenesis of inflammatory bowel disease (IBD), comprising:
obtaining blood samples from patients clinically diagnosed with IBD;
determining whether the gene variant and/or the genetic variant is present in each blood sample by contacting each blood sample with an allele-specific fluorescent-dye-labeled oligonucleotide probe targeting the gene variant and/or the genetic variant, and detecting whether allele-specific binding occurs between the gene variant and/or the genetic variant and the allele-specific fluorescent-dye-labeled oligonucleotide probe using allele-specific oligonucleotide hybridization assay;
using a *Saccharomyces cerevisiae* antigen to assay each blood sample to detect the presence of an anti-*Saccharomyces cerevisiae* antibody (Ab-ASCA) by detecting an antigen-antibody complex generated through binding between the Ab-ASCA and the *Saccharomyces cerevisiae* antigen;
using a *Pseudomonas fluorescens*-related sequence I2 antigen to assay each blood sample to detect the presence of an antibody to *Pseudomonas fluorescens*-related sequence I2 (Ab-I2) by detecting an antigen-antibody complex generated through binding between the Ab-I2 and the *Pseudomonas fluorescens*-related sequence I2 antigen;
using a *Escherichia coli* outer membrane porin C antigen to assay each blood sample to detect the presence of an antibody to *Escherichia coli* outer membrane porin C (Ab-OmpC) by detecting an antigen-antibody complex generated through binding between the Ab-OmpC and the *Escherichia coli* outer membrane porin C antigen;
using a neutrophil antigen to assay each blood sample to detect the presence of a perinuclear anti-neutrophil cytoplasmic antibody (Ab-pANCA) by detecting an antigen-antibody complex generated through binding between the Ab-pANCA and the neutrophil antigen;
determining each blood sample's immune expression profile based on the presence of Ab-ASCA, Ab-OmpC, Ab-I2 and/or Ab-pANCA;
stratifying IBD into one or more subdivisions based on the immune expression profiles of each blood sample;
performing a genetic association study by associating the presence of the gene variant and/or the genetic variant with the one or more subdivisions of IBD; and
determining the gene variant and/or the genetic variant as having involvement in the pathogenesis of IBD if the presence of the gene variant and/or the genetic variant is statistically significantly clustered around the one or more subdivisions of IBD.

2. The method of claim 1, wherein IBD is Crohn's disease (CD) or ulcerative colitis (UC).

3. The method of claim 1, wherein the genetic association study comprises a whole genome association study.

4. The method of claim 1, wherein the genetic association study comprises the use of a haplotype-defined gene structure.

5. The method of claim 1, wherein the genetic association study comprises the use of high throughput screening.

6. A method for determining whether a biological pathway has involvement in the pathogenesis of IBD, comprising:
obtaining blood samples from patients clinically diagnosed with IBD;
determining whether a genetic variant in the biological pathway is present in each blood sample by contacting each blood sample with an allele-specific fluorescent-dye-labeled oligonucleotide probe targeting the genetic variant, and detecting whether allele-specific binding occurs between the genetic variant and the allele-specific fluorescent-dye-labeled oligonucleotide probe using allele-specific oligonucleotide hybridization assay;
using a *Saccharomyces cerevisiae* antigen to assay each blood sample to detect the presence of an anti-*Saccharomyces cerevisiae* antibody (Ab-ASCA) by detecting an antigen-antibody complex generated through binding between the Ab-ASCA and the *Saccharomyces cerevisiae* antigen;
using a *Pseudomonas fluorescens*-related sequence I2 antigen to assay each blood sample to detect the presence of an antibody to *Pseudomonas fluorescens*-related sequence I2 (Ab-I2) by detecting an antigen-antibody complex generated through binding between the Ab-I2 and the *Pseudomonas fluorescens*-related sequence I2 antigen;

using a *Escherichia coli* outer membrane porin C antigen to assay each blood sample to detect the presence of an antibody to *Escherichia coli* outer membrane porin C (Ab-OmpC) by detecting an antigen-antibody complex generated through binding between the Ab-OmpC and the *Escherichia coli* outer membrane porin C antigen;

using a neutrophil antigen to assay each blood sample to detect the presence of a perinuclear anti-neutrophil cytoplasmic antibody (Ab-pANCA) by detecting an antigen-antibody complex generated through binding between the Ab-pANCA and the neutrophil antigen;

determining each blood sample's immune expression profile based on the presence of Ab-ASCA, Ab-OmpC, Ab-I2 and/or Ab-pANCA;

stratifying IBD into one or more subdivisions based on the immune expression profiles of each blood sample;

performing a genetic association study by associating the presence of the genetic variant with the one or more subdivisions of IBD; and determining the biological pathway as having involvement in the pathogenesis of IBD if the presence of the genetic variant is statistically significantly associated with the one or more subdivisions of IBD.

7. The method of claim 6, wherein IBD is Crohn's disease (CD).

8. The method of claim 6, wherein IBD is ulcerative colitis (UC).

* * * * *